US008470794B2

(12) United States Patent
Jayasena et al.

(10) Patent No.: US 8,470,794 B2
(45) Date of Patent: Jun. 25, 2013

(54) INCREASING ERYTHROPOIETIN USING NUCLEIC ACIDS HYBRIDIZABLE TO MICRO-RNA AND PRECURSORS THEREOF

(75) Inventors: Sumedha D. Jayasena, Thousand Oaks, CA (US); Susan Swift, Ojai, CA (US)

(73) Assignee: Amgen Inc., Thousand Oaks, CA (US)

( * ) Notice: Subject to any disclaimer, the term of this patent is extended or adjusted under 35 U.S.C. 154(b) by 5 days.

(21) Appl. No.: 12/681,160

(22) PCT Filed: Oct. 1, 2008

(86) PCT No.: PCT/US2008/011409

§ 371 (c)(1), (2), (4) Date: Aug. 10, 2010

(87) PCT Pub. No.: WO2009/045469

PCT Pub. Date: Apr. 9, 2009

(65) Prior Publication Data

US 2010/0296630 A1 Nov. 25, 2010

Related U.S. Application Data

(60) Provisional application No. 60/977,017, filed on Oct. 2, 2007.

(51) Int. Cl.
*C12N 15/11* (2006.01)

(52) U.S. Cl.
USPC .......... 514/44 A

(58) Field of Classification Search
USPC .......... 514/44 A
See application file for complete search history.

(56) References Cited

U.S. PATENT DOCUMENTS

| | | | | |
|---|---|---|---|---|
| 7,365,185 | B2 * | 4/2008 | Boukharov et al. | 536/24.1 |
| 2005/0261218 | A1 * | 11/2005 | Esau et al. | 514/44 |
| 2006/0265771 | A1 * | 11/2006 | Lewis et al. | 800/18 |
| 2009/0023670 | A1 * | 1/2009 | Sebestyen | 514/44 |
| 2009/0124566 | A1 * | 5/2009 | Chi et al. | 514/44 |

FOREIGN PATENT DOCUMENTS

WF WO 03/053997 7/2003

OTHER PUBLICATIONS

Sun et al. (Nucleic Acids Research) 2004, 32:e188, pp. 1-6.*

* cited by examiner

*Primary Examiner* — Brian Whiteman
(74) *Attorney, Agent, or Firm* — James E. Klaniecki

(57) ABSTRACT

Methods and compositions relating to nucleic acids targeting certain miRNA molecules are disclosed. The nucleic acids are useful, for example, in methods of increasing the expression and/or secretion of EPO and treating various disease states including anemia, hemophilia, and/or sickle cell disease.

28 Claims, 14 Drawing Sheets

SEQUENCE LISTING

```
<160> NUMBER OF SEQ ID NOS: 79

<210> SEQ ID NO 1
<211> LENGTH: 21
<212> TYPE: DNA
<213> ORGANISM: Homo sapiens

<400> SEQUENCE: 1

ttgggcatct aggcttgaac a                                              21


<210> SEQ ID NO 2
<211> LENGTH: 21
<212> TYPE: DNA
<213> ORGANISM: homo sapiens

<400> SEQUENCE: 2

tcgtcgtaac atgtcccgat a                                              21


<210> SEQ ID NO 3
<211> LENGTH: 21
<212> TYPE: DNA
<213> ORGANISM: homo sapiens

<400> SEQUENCE: 3

gttgccttag ggttttcgtc g                                              21
```

-continued

<210> SEQ ID NO 4
<211> LENGTH: 21
<212> TYPE: DNA
<213> ORGANISM: Homo sapiens

<400> SEQUENCE: 4
aggtcgagga tatactacgg a 21

<210> SEQ ID NO 5
<211> LENGTH: 21
<212> TYPE: DNA
<213> ORGANISM: Homo sapiens

<400> SEQUENCE: 5
ttcacgaagg aaaatctccc a 21

<210> SEQ ID NO 6
<211> LENGTH: 21
<212> TYPE: DNA
<213> ORGANISM: Homo sapiens

<400> SEQUENCE: 6
tgtttcacga agggaaatct c 21

<210> SEQ ID NO 7
<211> LENGTH: 21
<212> TYPE: DNA
<213> ORGANISM: Homo sapiens

<400> SEQUENCE: 7
gatgtttccc ttcgtgaaag a 21

<210> SEQ ID NO 8
<211> LENGTH: 19
<212> TYPE: DNA
<213> ORGANISM: Homo sapiens

<400> SEQUENCE: 8
ccaggtctcc cctctatcc 19

<210> SEQ ID NO 9
<211> LENGTH: 21
<212> TYPE: DNA
<213> ORGANISM: Homo sapiens

<400> SEQUENCE: 9
atacacccta ccatttaacg a 21

<210> SEQ ID NO 10
<211> LENGTH: 21
<212> TYPE: DNA
<213> ORGANISM: Homo sapiens

<400> SEQUENCE: 10
accaaatggc agggtgtatg t 21

<210> SEQ ID NO 11
<211> LENGTH: 21
<212> TYPE: DNA
<213> ORGANISM: Homo sapiens

<400> SEQUENCE: 11
aaagttcggt cccccgcaaa a 21

-continued

<210> SEQ ID NO 12
<211> LENGTH: 21
<212> TYPE: DNA
<213> ORGANISM: Homo sapiens

<400> SEQUENCE: 12
gagatctccc ttcgtgaaag a 21

<210> SEQ ID NO 13
<211> LENGTH: 21
<212> TYPE: DNA
<213> ORGANISM: Homo sapiens

<400> SEQUENCE: 13
actccatcat ccaacatatc a 21

<210> SEQ ID NO 14
<211> LENGTH: 16
<212> TYPE: DNA
<213> ORGANISM: Homo sapiens

<400> SEQUENCE: 14
actccatcat ccaaca 16

<210> SEQ ID NO 15
<211> LENGTH: 16
<212> TYPE: DNA
<213> ORGANISM: Homo sapiens

<400> SEQUENCE: 15
actccatcat caaaca 16

<210> SEQ ID NO 16
<211> LENGTH: 21
<212> TYPE: DNA
<213> ORGANISM: Homo sapiens

<400> SEQUENCE: 16
accttctgat cactaaaaca a 21

<210> SEQ ID NO 17
<211> LENGTH: 21
<212> TYPE: DNA
<213> ORGANISM: Homo sapiens

<400> SEQUENCE: 17
atttcgatct attggctttc a 21

<210> SEQ ID NO 18
<211> LENGTH: 21
<212> TYPE: DNA
<213> ORGANISM: Homo sapiens

<400> SEQUENCE: 18
acatttgtag gggctgacct t 21

<210> SEQ ID NO 19
<211> LENGTH: 21
<212> TYPE: DNA
<213> ORGANISM: Homo sapiens

<400> SEQUENCE: 19
atccgtcaca gtaatcgact a 21

<210> SEQ ID NO 20
<211> LENGTH: 21
<212> TYPE: DNA
<213> ORGANISM: Homo sapiens

<400> SEQUENCE: 20
actccatcat tcaacataac a 21

<210> SEQ ID NO 21
<211> LENGTH: 21
<212> TYPE: DNA
<213> ORGANISM: Homo sapiens

<400> SEQUENCE: 21
agtgtcactt ggccagagaa a 21

<210> SEQ ID NO 22
<211> LENGTH: 21
<212> TYPE: DNA
<213> ORGANISM: Homo sapiens

<400> SEQUENCE: 22
attgtcagat gtcggtacca g 21

<210> SEQ ID NO 23
<211> LENGTH: 21
<212> TYPE: DNA
<213> ORGANISM: Homo sapiens

<400> SEQUENCE: 23
ataccgaaaa gtaaggatac a 21

<210> SEQ ID NO 24
<211> LENGTH: 21
<212> TYPE: DNA
<213> ORGANISM: Homo sapiens

<400> SEQUENCE: 24
attagagtcg accgttgaca c 21

<210> SEQ ID NO 25
<211> LENGTH: 21
<212> TYPE: DNA
<213> ORGANISM: Homo sapiens

<400> SEQUENCE: 25
aacgtataca tcctacaggg t 21

<210> SEQ ID NO 26
<211> LENGTH: 21
<212> TYPE: DNA
<213> ORGANISM: Homo sapiens

<400> SEQUENCE: 26
acaaacgtct cctttgactc t 21

<210> SEQ ID NO 27
<211> LENGTH: 21
<212> TYPE: DNA
<213> ORGANISM: Homo sapiens

<400> SEQUENCE: 27
tcaccccttg ggaaggtact c 21

-continued

<210> SEQ ID NO 28
<211> LENGTH: 21
<212> TYPE: DNA
<213> ORGANISM: Homo sapiens

<400> SEQUENCE: 28
gtcgtcgtgt gacaccaaac a 21

<210> SEQ ID NO 29
<211> LENGTH: 21
<212> TYPE: DNA
<213> ORGANISM: Homo sapiens

<400> SEQUENCE: 29
tttcacgaag gaaaatctcc c 21

<210> SEQ ID NO 30
<211> LENGTH: 20
<212> TYPE: DNA
<213> ORGANISM: Homo sapiens

<400> SEQUENCE: 30
gccctttcat cattgcactg 20

<210> SEQ ID NO 31
<211> LENGTH: 20
<212> TYPE: DNA
<213> ORGANISM: Homo sapiens

<400> SEQUENCE: 31
gtagtgcttt ctactttatg 20

<210> SEQ ID NO 32
<211> LENGTH: 20
<212> TYPE: DNA
<213> ORGANISM: Homo sapiens

<400> SEQUENCE: 32
cgggactttg agggccagtt 20

<210> SEQ ID NO 33
<211> LENGTH: 20
<212> TYPE: DNA
<213> ORGANISM: Homo sapiens

<400> SEQUENCE: 33
acccacagac gtaccaatca 20

<210> SEQ ID NO 34
<211> LENGTH: 20
<212> TYPE: DNA
<213> ORGANISM: Homo sapiens

<400> SEQUENCE: 34
cctctatagg gaagcgcgtt 20

<210> SEQ ID NO 35
<211> LENGTH: 20
<212> TYPE: DNA
<213> ORGANISM: Homo sapiens

<400> SEQUENCE: 35
gaaagtgcat ccctctggag 20

<210> SEQ ID NO 36
<211> LENGTH: 20
<212> TYPE: DNA
<213> ORGANISM: Homo sapiens

<400> SEQUENCE: 36
gaaagtgctt ccctctagag 20

<210> SEQ ID NO 37
<211> LENGTH: 20
<212> TYPE: DNA
<213> ORGANISM: Homo sapiens

<400> SEQUENCE: 37
gaaagcgctt ccctctagag 20

<210> SEQ ID NO 38
<211> LENGTH: 20
<212> TYPE: DNA
<213> ORGANISM: Homo sapiens

<400> SEQUENCE: 38
ctctaaaggg gagcgctttg 20

<210> SEQ ID NO 39
<211> LENGTH: 21
<212> TYPE: RNA
<213> ORGANISM: Homo sapiens

<400> SEQUENCE: 39
aacccguaga uccgaacuug u 21

<210> SEQ ID NO 40
<211> LENGTH: 21
<212> TYPE: RNA
<213> ORGANISM: Homo sapiens

<400> SEQUENCE: 40
agcagcauug uacagggcua u 21

<210> SEQ ID NO 41
<211> LENGTH: 21
<212> TYPE: RNA
<213> ORGANISM: Homo sapiens

<400> SEQUENCE: 41
agcagcauug uacagggcua u 21

<210> SEQ ID NO 42
<211> LENGTH: 21
<212> TYPE: RNA
<213> ORGANISM: Homo sapiens

<400> SEQUENCE: 42
caacggaauc ccaaaagcag c 21

<210> SEQ ID NO 43
<211> LENGTH: 21
<212> TYPE: RNA
<213> ORGANISM: Homo sapiens

<400> SEQUENCE: 43
uccagcuccu auaugaugcc u 21

<210> SEQ ID NO 44
<211> LENGTH: 21
<212> TYPE: RNA
<213> ORGANISM: Homo sapiens

<400> SEQUENCE: 44
aagugcuucc uuuuagaggg u 21

<210> SEQ ID NO 45
<211> LENGTH: 21
<212> TYPE: RNA
<213> ORGANISM: Homo sapiens

<400> SEQUENCE: 45
acaaagugcu ucccuuuaga g 21

<210> SEQ ID NO 46
<211> LENGTH: 21
<212> TYPE: RNA
<213> ORGANISM: Homo sapiens

<400> SEQUENCE: 46
cuacaaaggg aagcacuuuc u 21

<210> SEQ ID NO 47
<211> LENGTH: 19
<212> TYPE: RNA
<213> ORGANISM: Homo sapiens

<400> SEQUENCE: 47
gguccagagg ggagauagg 19

<210> SEQ ID NO 48
<211> LENGTH: 21
<212> TYPE: RNA
<213> ORGANISM: Homo sapiens

<400> SEQUENCE: 48
uaugugggau gguaaaccgc u 21

<210> SEQ ID NO 49
<211> LENGTH: 21
<212> TYPE: RNA
<213> ORGANISM: Homo sapiens

<400> SEQUENCE: 49
ugguuuaccg ucccacauac a 21

<210> SEQ ID NO 50
<211> LENGTH: 21
<212> TYPE: RNA
<213> ORGANISM: Homo sapiens

<400> SEQUENCE: 50
uuucaagcca gggggcguuu u 21

<210> SEQ ID NO 51
<211> LENGTH: 21
<212> TYPE: RNA
<213> ORGANISM: Homo sapiens

<400> SEQUENCE: 51
cucuagaggg aagcacuuuc u 21

-continued

<210> SEQ ID NO 52
<211> LENGTH: 21
<212> TYPE: RNA
<213> ORGANISM: Homo sapiens

<400> SEQUENCE: 52
ugagguagua gguuguauag u 21

<210> SEQ ID NO 53
<211> LENGTH: 16
<212> TYPE: RNA
<213> ORGANISM: Homo sapiens

<400> SEQUENCE: 53
ugagguagua gguugu 16

<210> SEQ ID NO 54
<211> LENGTH: 16
<212> TYPE: RNA
<213> ORGANISM: Homo sapiens

<400> SEQUENCE: 54
ugagguagua guuugu 16

<210> SEQ ID NO 55
<211> LENGTH: 21
<212> TYPE: RNA
<213> ORGANISM: Homo sapiens

<400> SEQUENCE: 55
uggaagacua gugauuuugu u 21

<210> SEQ ID NO 56
<211> LENGTH: 21
<212> TYPE: RNA
<213> ORGANISM: Homo sapiens

<400> SEQUENCE: 56
uaaagcuaga uaaccgaaag u 21

<210> SEQ ID NO 57
<211> LENGTH: 21
<212> TYPE: RNA
<213> ORGANISM: Homo sapiens

<400> SEQUENCE: 57
uguaaacauc cccgacugga a 21

<210> SEQ ID NO 58
<211> LENGTH: 21
<212> TYPE: RNA
<213> ORGANISM: Homo sapiens

<400> SEQUENCE: 58
uaggcagugu cauuagcuga u 21

<210> SEQ ID NO 59
<211> LENGTH: 21
<212> TYPE: RNA
<213> ORGANISM: Homo sapiens

<400> SEQUENCE: 59
ugagguagua aguuguauug u 21

-continued

<210> SEQ ID NO 60
<211> LENGTH: 21
<212> TYPE: RNA
<213> ORGANISM: Homo sapiens

<400> SEQUENCE: 60
ucacagugaa ccggucucuu u 21

<210> SEQ ID NO 61
<211> LENGTH: 21
<212> TYPE: RNA
<213> ORGANISM: Homo sapiens

<400> SEQUENCE: 61
uaacagucua cagccauggu c 21

<210> SEQ ID NO 62
<211> LENGTH: 21
<212> TYPE: RNA
<213> ORGANISM: Homo sapiens

<400> SEQUENCE: 62
uauggcuuuu cauuccuaug u 21

<210> SEQ ID NO 63
<211> LENGTH: 21
<212> TYPE: RNA
<213> ORGANISM: Homo sapiens

<400> SEQUENCE: 63
uaaucucagc uggcaacugu g 21

<210> SEQ ID NO 64
<211> LENGTH: 21
<212> TYPE: RNA
<213> ORGANISM: Homo sapiens

<400> SEQUENCE: 64
uugcauaugu aggaugucccc a 21

<210> SEQ ID NO 65
<211> LENGTH: 21
<212> TYPE: RNA
<213> ORGANISM: Homo sapiens

<400> SEQUENCE: 65
uguuugcaga ggaaacugag a 21

<210> SEQ ID NO 66
<211> LENGTH: 21
<212> TYPE: RNA
<213> ORGANISM: Homo sapiens

<400> SEQUENCE: 66
aguggggaac ccuuccauga g 21

<210> SEQ ID NO 67
<211> LENGTH: 21
<212> TYPE: RNA
<213> ORGANISM: Homo sapiens

<400> SEQUENCE: 67
cagcagcaca cugugguuug u 21

<210> SEQ ID NO 68
<211> LENGTH: 21
<212> TYPE: RNA
<213> ORGANISM: Homo sapiens

<400> SEQUENCE: 68
aaagugcuuc cuuuuagagg g 21

<210> SEQ ID NO 69
<211> LENGTH: 21
<212> TYPE: RNA
<213> ORGANISM: Homo sapiens

<400> SEQUENCE: 69
cagugcaaug augaaagggc a 21

<210> SEQ ID NO 70
<211> LENGTH: 20
<212> TYPE: RNA
<213> ORGANISM: Homo sapiens

<400> SEQUENCE: 70
cauaaaguag aaagcacuac 20

<210> SEQ ID NO 71
<211> LENGTH: 21
<212> TYPE: RNA
<213> ORGANISM: Homo sapiens

<400> SEQUENCE: 71
aacuggcccu caaagucccg c 21

<210> SEQ ID NO 72
<211> LENGTH: 21
<212> TYPE: RNA
<213> ORGANISM: Homo sapiens

<400> SEQUENCE: 72
ugauugguac gucugugggu a 21

<210> SEQ ID NO 73
<211> LENGTH: 21
<212> TYPE: RNA
<213> ORGANISM: Homo sapiens

<400> SEQUENCE: 73
aacgcgcuuc ccuauagagg g 21

<210> SEQ ID NO 74
<211> LENGTH: 21
<212> TYPE: RNA
<213> ORGANISM: Homo sapiens

<400> SEQUENCE: 74
cuccagaggg augcacuuuc u 21

<210> SEQ ID NO 75
<211> LENGTH: 21
<212> TYPE: RNA
<213> ORGANISM: Homo sapiens

<400> SEQUENCE: 75
cucuagaggg aagcacuuuc u 21

-continued

```
<210> SEQ ID NO 76
<211> LENGTH: 21
<212> TYPE: RNA
<213> ORGANISM: Homo sapiens

<400> SEQUENCE: 76

cucuagaggg aagcgcuuuc u                                              21


<210> SEQ ID NO 77
<211> LENGTH: 21
<212> TYPE: RNA
<213> ORGANISM: Homo sapiens

<400> SEQUENCE: 77

caaagcgcuc cccuuuagag g                                              21


<210> SEQ ID NO 78
<211> LENGTH: 14
<212> TYPE: RNA
<213> ORGANISM: Homo sapiens

<400> SEQUENCE: 78

ccguacaaug cugc                                                      14


<210> SEQ ID NO 79
<211> LENGTH: 12
<212> TYPE: RNA
<213> ORGANISM: Homo sapiens

<400> SEQUENCE: 79

cgcucccuug ag                                                        12
```

INCREASING ERYTHROPOIETIN USING NUCLEIC ACIDS HYBRIDIZABLE TO MICRO-RNA AND PRECURSORS THEREOF

CROSS-REFERENCES TO RELATED APPLICATIONS

This application is a national stage application under 35 U.S.C. §371 of International Application No. PCT/US2008/011409, having an international filing date of Oct. 1, 2008; which claims the benefit of U.S. provisional application Ser. No. 60/977,017, filed Oct. 1, 2007, which is hereby incorporated by reference.

REFERENCE TO THE SEQUENCE LISTING

The present application is being filed along with a Sequence Listing in electronic format. The Sequence Listing is provided as a file entitled A-1366-US-PCT_seq_listing.txt., created Mar. 30, 2010, which is 11.6 KB in size. The information in the electronic format of the Sequence Listing is incorporated herein by reference in its entirety.

BACKGROUND

MicroRNAs (miRNAs) regulate gene expression through an RNA interference (RNAi) mechanism by targeting specific messages and inhibiting their translation. The genes encoding miRNAs are longer than the processed miRNA molecule. miRNAs are first transcribed as primary transcripts or pri-miRNA and processed to short, approximately 70-nucleotide stem-loop structures known as pre-miRNA in the cell nucleus. This processing is performed in humans by a protein complex known as the Microprocessor complex, including the nuclease Drosha and the double-stranded RNA binding protein DGCR8. These pre-miRNAs are then processed to mature miRNAs in the cytoplasm by interaction with the endonuclease Dicer assisted by TRBP, which also initiates the formation of the RNA-induced silencing complex (RISC). This complex is responsible for the gene silencing observed due to miRNA expression and RNA interference. The pathway in plants varies slightly due to their lack of Drosha homologs. Instead, Dicer homologs alone affect several processing steps.

Efficient processing of pri-miRNA by Drosha requires the presence of extended single-stranded RNA on both 3'- and 5'-ends of a hairpin molecule. The Drosha complex cleaves RNA molecules at approximately two helical turns away from the terminal loop and approximately one turn away from basal segments. In most analyzed molecules this region contains unpaired nucleotides and the free energy of the duplex is relatively high compared to lower and upper stem regions. The resulting pre-miRNA has a short hairpin loop structure and is exported to the cytoplasm by Exportin 5 with help from cofactor Ran, a GTPase (Gwizdek et al., J. Biol. Chem. 278, 5505-8 (2003); Lund et al., Science 303, 95-8 (2004); Bohnsack et al., RNA 10, 185-91 (2004)).

When Dicer cleaves the pre-miRNA stem-loop in the cytoplasm, two complementary short RNA molecules are formed, but only one is integrated into the RISC complex on the basis of the stability of the 5' end. The remaining strand, known as the passenger strand is degraded. After integration into the active RISC complex, miRNAs base pair with their complementary mRNA molecules and induce down regulation of the expression of the transcript by one of the two key mechanisms, depending on the degree of complementarity between the miRNA and the target mRNA. In animals, pairing between miRNA and their target mRNAs is not usually perfect, although there are a few exceptions where perfect or near perfect recognition exist (Yekta et al., Science 304, 594-6 (2004); Mansfield et al. Nat Genet 36, 1079-83 (2004)). If the complementarity between the miRNA and the target is perfect or near perfect, then the cleavage of the mRNA is mediated by the endonuclease (slicer) activity in the RISC provided by Ago2 protein. Where miRNAs bind to their targets via imperfect base pairing, miRNA bound messages may be directed to a cytoplasmic foci known as P-bodies or processing bodies where the ribosomes are depleted but rich in nucleases (Parker et al., Nature Structural & Molecular Biology 11, 121-12 (2004)). P-bodies serve as either degradation centers or storage depots for these messages, where their translation is inhibited.

To date, close to 500 miRNAs have been identified in humans (Griffiths-Jones, S. Nucleic Acids Res 32, D109-11 (2004)). Bioinformatics approaches have predicted that these miRNAs are capable of regulating at least 30% of human transcripts (Lewis, et al. Cell, 2005. 120(1): p. 15-20). As a result, miRNAs have the potential to play a vital role in many biological processes whose deregulation could lead to various disease states. Experimental evidence is accumulating to elucidate their roles in many biological processes. These attributes make miRNAs a potential class of targets for therapeutic intervention. However, the lack of current understanding on specific roles played by individual miRNAs in a plethora of biological processes has complicated the targeting of miRNAs.

Erythropoietin (EPO) is a glycoprotein hormone involved in the maturation of erythroid progenitor cells into erythrocytes. It is essential in regulating levels of red blood cells in circulation. Naturally occurring erythropoietin is produced by the liver during fetal life and by the kidney of adults. EPO circulates in the blood and stimulates the production of red blood cells in bone marrow. Anemia is almost invariably a consequence of renal failure due to decreased production of erythropoietin from the kidney. Recombinant erythropoietin produced by genetic engineering techniques involving the expression of a protein product from a host cell transformed with the gene encoding erythropoietin has been found to be effective when used in the treatment of anemia resulting from chronic renal failure.

Vascular endothelial growth factor (VEGF) is a positive regulator of angiogenesis. Hua et al., MiRNA-Directed Regulation of VEGF and Other Angiogenic Factors under Hypoxia, PloS ONE 1(1): e116, 1-13, 2 (2006). VEGF is a highly specific mitogen for vascular endothelial cells. Neufeld, Cohen et al., Vascular Endothelial Growth Factor (VEGF) and Its Receptors, FASEB J. 13, 9-22 (1999).

Low levels of erythropoietin are normally present in human urine, while individuals suffering from aplastic anemia exhibit elevated levels of urinary erythropoietin. The purification of human urinary erythropoietin by Miyake et al. in J. Biol. Chem., 252, 5558 (1977), used, as starting material, urine from aplastic anemic individuals. To date, however, urinary erythropoietin has not been shown to be therapeutically useful.

The identification, cloning, and expression of genes encoding erythropoietin are described in U.S. Pat. No. 4,703,008 to Lin. A description of a method for purification of recombinant erythropoietin from cell medium is included in U.S. Pat. No. 4,667,016 to Lai et al. The expression and recovery of biologically active recombinant erythropoietin from mammalian cell hosts containing the erythropoietin gene on recombinant plasmids has, for the first time, made available quantities of erythropoietin suitable for therapeutic applications. In addition, knowledge of the gene sequence and the availability of larger quantities of purified protein have led to a better understanding of the mode of action of this protein.

Given the known therapeutic benefits of EPO, methods of increasing EPO expression or secretion of EPO would be of great benefit to patients in need of EPO therapy. The methods and compositions described herein address these and other needs in the art.

SUMMARY

Figure 1A:
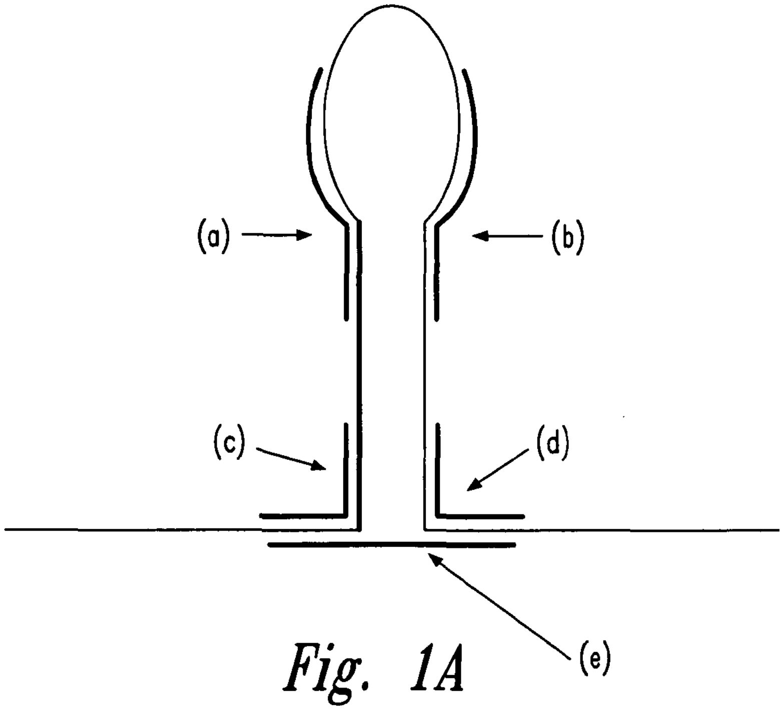
FIG. 1 illustrates examples of target regions of miRNA precursors.

It has been discovered that nucleic acid sequences designed to hybridize to certain miRNAs and precursors thereof are useful in increasing the expression of select genes, such as but not limited to the expression and/or secretion of erythropoietin ("EPO") in cells, treating diseases such as anemia, hemophilia, and sickle cell disease, as well as increasing erythropoiesis, or increasing erythropoietin levels in patients in need thereof.

In one aspect, a method is provided for increasing the expression and/or secretion of EPO. The method includes introducing into the cell a nucleic acid that is hybridizable to an RNA molecule, is antisense to an RNA molecule, is substantially complimentary to an RNA molecule, and/or has a sequence with at least 70% sequence identity to a 6 or more nucleobase (or nucleotide) sequence (e.g. contiguous sequence) of one of SEQ ID NOs: 1-38 (also referred to herein as "anti-miRNA nucleic acid sequences"). The nucleic acid sequences of SEQ ID NOs: 1-38 hybridize to the target miRNA sequences of SEQ ID NOs: 39-77, as shown in Table 3.

The RNA molecule mentioned above may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof. See Table 3 for the sequences of the mature miRNAs, which serve as target miRNAs.

In another aspect, a method is provided for enhancing erythropoiesis in a subject, increasing EPO levels in a subject, or treating a subject in need thereof for anemia, hemophilia, or sickle cell disease. The method includes administering to the subject an effective amount of a nucleic acid that is hybridizable to an RNA molecule, is antisense to an RNA molecule, is substantially complimentary to an RNA molecule, and/or has a sequence with at least 70% sequence identity to a 6 or more nucleobase (or nucleotide) sequence (e.g. contiguous sequence) of one of SEQ ID NOs: 1-38. The RNA molecule may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof. In another aspect, a nucleic acid is provided having at least 90% locked nucleic acid units. The nucleic acid is hybridizable to an RNA molecule, is antisense to an RNA molecule, is substantially complimentary to an RNA molecule, and/or has a sequence with at least 70% sequence identity to a 6 or more nucleobase (or nucleotide) sequence (e.g. contiguous sequence) of one of SEQ ID NOs: 1-38. The RNA molecule may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof. DETAILED DESCRIPTION OF THE INVENTION

I. Definitions

As used herein, "nucleic acid" means single-, double-, or multiple-stranded DNA, RNA and derivatives thereof. In certain embodiments, the nucleic acid is single stranded. Modifications may include those that provide other chemical groups that incorporate additional charge, polarizability, hydrogen bonding, electrostatic interaction, and functionality to the nucleic acid. Such modifications include, but are not limited to, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping moieties. A 2'deoxy nucleic acid linker is a divalent nucleic acid of any appropriate length and/or internucleotide linkage wherein the nucleotides are 2'deoxy nucleotides. A "nucleobase" refers to the portion(s) of a nucleic acid involved in hybridization (base pairing), and includes, but is not limited to, nitrogenous bases such as cytosine, guanine, adenine, thymine, uracil, and derivatives thereof A "nucleic acid unit," as used herein, refers to the portions of a nucleic acid that are linked together by internucleotide linkages, and contain a nucleobase (e.g. a nucleoside).

Certain nucleic aid compounds can exist in unsolvated forms as well as solvated forms, including hydrated forms. In general, the solvated forms are equivalent to unsolvated forms. Certain nucleic aid compounds may exist in multiple crystalline or amorphous forms. In general, all physical forms are equivalent for the uses contemplated by the methods provided herein.

Certain nucleic aid compounds may possess asymmetric carbon atoms (optical centers) or double bonds; the racemates, diastereomers, geometric isomers and individual isomers.

The nucleic aid compounds may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$) or carbon-14 ($^{14}C$).

As used herein, the term "miRNA precursor," or "precursor thereof" in reference to a particular miRNA refers broadly to any precursor which through processing in a cell results in the specified miRNA. The term thus includes the corresponding pri-miRNA, pre-miRNA or variant thereof. In some embodiments, the precursor is the corresponding pri-miRNA or pre-miRNA. The pre-miRNA sequence may include, for example, from 45-90, 60-80 or 60-70 nucleotides. The sequence of the pre-miRNA may include the entire miRNA sequence, or be that of a pri-miRNA excluding from 0-160 nucleotides from the 5' and 3' ends of the pri-miRNA. The sequence of the pre-miRNA may comprise the sequence of a hairpin loop. The pri-miRNA sequence may comprise from 45-250, 55-200, 70-150 or 80-100 nucleotides. The sequence of the pri-miRNA may include the pre-miRNA or miRNA as set forth in Table 3 below. The pri-miRNA may also include a hairpin structure (e.g. from 37-50 nucleotides). For example, miR-103-1,2 (SEQ ID NO:40) and miR-107 (SEQ ID NO:41) have the same primary sequence (see Table 3), but can have different precursors.

The terms "hybridization" or "hybridizable" refer to the pairing of complementary strands of nucleic acids, including triple-stranded nucleic acid hybridization. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances.

The phrases "specifically hybridizable" or "hybridizes specifically to" and other similar phrases refer to the association of a nucleic acid with an miRNA, or miRNA precursor, resulting in interference with the normal function of the miRNA, or miRNA precursor (e.g. by altering the activity, disrupting the function, or modulating the level of the miRNA or miRNA precursor). Where a nucleic acid is "specifically hybridizable," to an miRNA or miRNA precursor, there is a sufficient degree of complementarity to avoid non-specific binding of the nucleic acid to nucleic acid sequences other than the intended miRNA or miRNA precursor under conditions in which specific hybridization is desired (e.g. under physiological conditions in the case of in vivo assays or therapeutic treatment, and under standard assay conditions in the case of in vitro assays). The sequence of the nucleic acid need not be 100% complementary to that of its target miRNA or miRNA precursor to be specifically hybridizable. Moreover, the nucleic acid may hybridize over one or more segments of the miRNA or miRNA precursor such that intervening or adjacent segments are not involved in the hybridization (e.g., a bulge, a loop structure or a hairpin structure).

The term "stringent hybridization conditions" or "stringent conditions" refers to conditions under which a nucleic acid hybridizes to an miRNA or miRNA precursor to form a stable complex (e.g. a duplex), but to a minimal number of other sequences. The stability of complex is a function of salt concentration and temperature (See, for example, Sambrook et al., Molecular Cloning: A Laboratory Manual 2d Ed. (Cold Spring Harbor Laboratory, (1989); incorporated herein by reference). Stringency levels used to hybridize a nucleic acid to an miRNA or miRNA precursor can be readily varied by those of skill in the art. The phrase "low stringency hybridization conditions" refers to conditions equivalent to hybridization in 10% formamide, 5 times Denhart's solution, 6 times SSPE, 0.2% SDS at 42° C., followed by washing in 1 times SSPE, 0.2% SDS, at 50° C. Denhart's solution and SSPE are well known to those of skill in the art as are other suitable hybridization buffers. (See, e.g., Sambrook et al.). The term "moderately stringent hybridization conditions" refers to conditions equivalent to hybridization in 50% formamide, 5 times Denhart's solution, 5 times SSPE, 0.2% SDS at 42° C., followed by washing in 0.2 times SSPE, 0.2% SDS, at 60° C. The term "highly stringent hybridization conditions" refers to conditions equivalent to hybridization in 50% formamide, 5 times Denhart's solution, 5 times SSPE, 0.2% SDS at 42° C., followed by washing in 0.2 times SSPE, 0.2% SDS, at 65° C.

"Complementary," as used herein, refers to the capacity for precise pairing of two nucleobases (e.g. A to T (or U), and G to C) regardless of where in the nucleic acid or miRNA or miRNA precursor the two are located. For example, if a nucleobases at a certain position of nucleic acid is capable of hydrogen bonding with a nucleobases at a certain position of an miRNA or miRNA precursor, then the position of hydrogen bonding between the nucleic acid and the miRNA or miRNA precursor is considered to be a complementary position. The nucleic acid and miRNA or miRNA precursor are "substantially complementary" to each other when a sufficient number of complementary positions in each molecule are occupied by nucleobases that can hydrogen bond with each other. Thus, the term "substantially complementary" is used to indicate a sufficient degree of precise pairing over a sufficient number of nucleobases such that stable and specific binding occurs between the nucleic acid and an miRNA or miRNA precursor. The phrase "substantially complementary" thus means that there may be one or more mismatches between the nucleic acid and the miRNA or miRNA precursor when they are aligned, provided that stable and specific binding occurs. The term "mismatch" refers to a site at which a nucleobases in the nucleic acid and a nucleobases in the miRNA or precursor with which it is aligned are not complementary. The nucleic acid and miRNA or miRNA precursor are "perfectly complementary" to each other when the nucleic acid is fully complementary to the miRNA or miRNA precursor across the entire length of the nucleic acid.

Generally, a nucleic acid is "antisense" to an miRNA or miRNA precursor when, written in the 5' to 3' direction, it comprises the reverse complement of the corresponding region of the target nucleic acid. "Antisense compounds" are also often defined in the art to comprise the further limitation of, once hybridized to a target, being able to modulate levels, expression or function of the target compound.

As used herein, "sequence identity" or "identity" refers to the nucleobases in two sequences that are the same when aligned for maximum correspondence over a specified comparison window. As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "pharmaceutically acceptable salts" is meant to include salts of the active compounds which are prepared with relatively nontoxic acids or bases, depending on the particular substituents found on the compounds described herein. When nucleic aid compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When nucleic aid compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", J. Pharm. Sci., 1977, 66, 1-19). Certain nucleic aid compounds contain both basic and acidic functionalities that allow the compounds to be converted into either base or acid addition salts.

The neutral forms of the nucleic aid compounds may be regenerated by contacting the salt with a base or acid and isolating the parent compound in the conventional manner. The parent form of the compound differs from the various salt forms in certain physical properties, such as solubility in polar solvents.

In addition to salt forms, nucleic aid compounds are provided which are in a prodrug form. Prodrugs of the nucleic acids described herein are those compounds that readily undergo chemical changes under physiological. Additionally, prodrugs can be converted to the nucleic acids by chemical or biochemical methods in an ex vivo environment. For example, prodrugs can be slowly converted to the nucleic acids when placed in a transdermal patch reservoir with a suitable enzyme or chemical reagent.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

The term "anemia" refers to deficiencies of red blood cells and/or hemoglobin, resulting in a reduced ability of blood to transfer oxygen to the tissues. This includes anemia resulting from a host of conditions such as decline or loss of kidney function (e.g. chronic renal failure, acute renal failure, and end-stage renal disease), myelosuppressive therapy, such as chemotherapeutic or anti-viral drugs (such as AZT), progression of non-myeloid cancers, and viral infections (such as HIV).

As used herein "combination therapy" or "adjunct therapy" means that the patient in need of the drug is treated or given another drug for the disease in conjunction with the nucleic acid. This combination therapy can be sequential therapy where the patient is treated first with one drug and then the other or the two drugs are given simultaneously.

"Patient" refers to a mammalian subject (e.g. human).

II. Overview

Various methods and compositions are provided herein based, in part, upon the identification of certain miRNAs that are involved in decreasing the expression and/or secretion of EPO. Anti-miRNA nucleic acids that are capable of hybridizing to these identified miRNAs and thus increasing the expression and/or secretion of proteins such as EPO are useful in the treatment of certain disease states such as anemia. The miRNAs found to be involved in decreasing EPO expression and/or secretion include miRNA molecules comprising an miRNA sequence of miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof. See Table 3 for the sequences of the mature miRNAs.

Disclosed herein are nucleic acids with particular sequences and chemical structure that can hybridize to these miRNAs and thus inhibit their activity, such as SEQ ID NOs: 1-38, as variously defined herein. Pharmaceutical compositions containing these nucleic acids are also provided. These nucleic acids and compositions can be used to increase the expression of EPO in a cell and/or secretion of EPO protein from the cell, as well as to treat diseases such as anemia, hemophilia, or sickle cell disease, increasing erythropoiesis, and/or increasing erythropoietin levels.

III. Increasing Expression or Secretion of EPO

Methods for increasing the expression and/or secretion of EPO protein by a cell include introducing into the cell a nucleic acid hybridizable to an RNA molecule, such nucleic acid also being referred to herein as an anti-miRNA nucleic acid.

Target RNA molecules may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-P (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof. In some embodiments the RNA molecule may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77). See Table 3 for the sequences of the mature miRNAs.

In some embodiments, the RNA molecule may comprise an miRNA selected from let-7-a-1,2,3 (SEQ ID NO:52), let-7-b,c (SEQ ID NO:53), let-7-g-I (SEQ ID NO:54), miR-100 (SEQ ID NO:39), miR-103-1,2 (SEQ ID NO:40), miR-128-a,b (SEQ ID NO:60), miR-191 (SEQ ID NO:42), miR-299-5p (SEQ ID NO:49), miR-30-d (SEQ ID NO:57), miR-337 (SEQ ID NO:43), miR-34-b (SEQ ID NO:58), miR-520-g,h (SEQ ID NO:45), miR-524* (SEQ ID NO:46), miR-7-1,2,3 (SEQ ID NO:55), miR-9*-1,2,3 (SEQ ID NO:56), miR-98 (SEQ ID NO:59), and precursors thereof. The RNA molecule may also comprise an miRNA selected from let-7-a-1,2,3 (SEQ ID NO:52), let-7-b,c (SEQ ID NO:53), let-7-g-I (SEQ ID NO:54), miR-100 (SEQ ID NO:39), miR-103-1,2 (SEQ ID NO:40), miR-128-a,b (SEQ ID NO:60), miR-191 (SEQ ID NO:42), miR-30-d (SEQ ID NO:57), miR-337 (SEQ ID NO:43), miR-34-b (SEQ ID NO:58), miR-520-g,h (SEQ ID NO:45), miR-524* (SEQ ID NO:46), miR-7-1,2,3 (SEQ ID NO:55), miR-9*-1,2,3 (SEQ ID NO:56), and precursors thereof. The RNA molecule may also comprise an miRNA selected from let-7-a-1,2,3 (SEQ ID NO:52), let-7-b,c (SEQ ID NO:53), let-7-g-I (SEQ ID NO:54), miR-100 (SEQ ID NO:39), miR-103-1,2 (SEQ ID NO:40), miR-30-d (SEQ ID NO:57), miR-34-b (SEQ ID NO:58), miR-524* (SEQ ID NO:46), miR-7-1,2,3 (SEQ ID NO:55), miR-9*-1,2,3 (SEQ ID NO:56), and precursors thereof. The RNA molecule may also comprise an miRNA selected from let-7-g-I (SEQ ID NO:54), miR-103-1,2 (SEQ ID NO:40), miR-34-b (SEQ ID NO:58), and precursors thereof In some embodiments, the RNA molecule comprises miR-103-1,2 (SEQ ID NO:40), or precursor thereof.

In other embodiments, the RNA molecule may comprise an miRNA selected from miR-100 (SEQ ID NO:39), miR-103-1,2 (SEQ ID NO:40), miR-107 (SEQ ID NO:41), miR-191 (SEQ ID NO:42), miR-337 (SEQ ID NO:43), miR-520-f (SEQ ID NO:44), miR-520-g,h (SEQ ID NO:45), miR-524* (SEQ ID NO:46), miR-198 (SEQ ID NO:47), miR-299-3p (SEQ ID NO:48), miR-299-5p (SEQ ID NO:49), miR-498 (SEQ ID NO:50), miR-518-f* (SEQ ID NO:51) and precursors thereof. The RNA molecule may also comprise miR-100 (SEQ ID NO:39), miR-103-1,2 (SEQ ID NO:40), miR-107 (SEQ ID NO:41), miR-191 (SEQ ID NO:42), miR-337 (SEQ ID NO:43), miR-520-f (SEQ ID NO:44), miR-520-g,h (SEQ ID NO:45), miR-524* (SEQ ID NO:46), or precursors thereof. In some embodiments, the RNA molecule may comprise miR-100 (SEQ ID NO:39), miR-103-1,2 (SEQ ID NO:40), miR-107 (SEQ ID NO:41), miR-337 (SEQ ID NO:43), miR-524* (SEQ ID NO:46), or precursors thereof. The RNA molecule may also comprise miR-103-1,2 (SEQ ID NO:40), miR-107 (SEQ ID NO:41), miR-524* (SEQ ID NO:46), or precursors thereof; miR-100 (SEQ ID NO:39), miR-103-1,2 (SEQ ID NO:40), miR-107 (SEQ ID NO:41), miR-191 (SEQ ID NO:42), miR-337 (SEQ ID NO:43), miR-524* (SEQ ID NO:46), or precursors thereof; miR-100 (SEQ ID NO:39), miR-103-1,2 (SEQ ID NO:40), miR-107 (SEQ ID NO:41), or precursors thereof; miR-337 (SEQ ID NO:43), miR-198 (SEQ ID NO:47), miR-299-3p (SEQ ID NO:48), miR-299-5p (SEQ ID NO:49), miR-498 (SEQ ID NO:50), miR-518-f* (SEQ ID NO:51), or precursors thereof; miR-337 (SEQ ID NO:43), miR-299-5p (SEQ ID NO:49), or precursors thereof; or simply miR-337 (SEQ ID NO:43), or precursors thereof.

The increase in expression and/or secretion of EPO is relative to the expression and/or secretion of EPO by a cell in the absence of the nucleic acid. Thus, an effective amount of the nucleic acid is introduced to the cell to result in the increase in the expression and/or secretion of EPO by a cell.

The sequence of the nucleic acid may be designed such that it will hybridize to a particular miRNA or miRNA precursor or a region or segment thereof. "Targeting" thus includes determination of at least one target region, segment, or site within the target miRNA or miRNA precursor for the interaction to occur such that the desired effect, e.g., modulation of levels, expression or function, will result. As used herein, the term "region" or "target region" is defined as a portion of the target miRNA or miRNA precursor having at least one identifiable sequence, structure, function, or characteristic.

In some embodiments, a nucleic acid is designed to hybridize to a single continuous region within any appropriate portion of the target miRNA. See FIG. 1A and FIG. 1B. The contiguous region may be 6, 7, 8, 9, 10, 11, 12, 13, 14, 15, 16, 17, 18, 19, 20, or 21 nucleotides in length. In other embodiments, a single nucleic acid is designed to bind to two different contiguous regions of a target miRNA or miRNA precursor. See FIG. 1A nucleic acid (e).

Figure 1B:
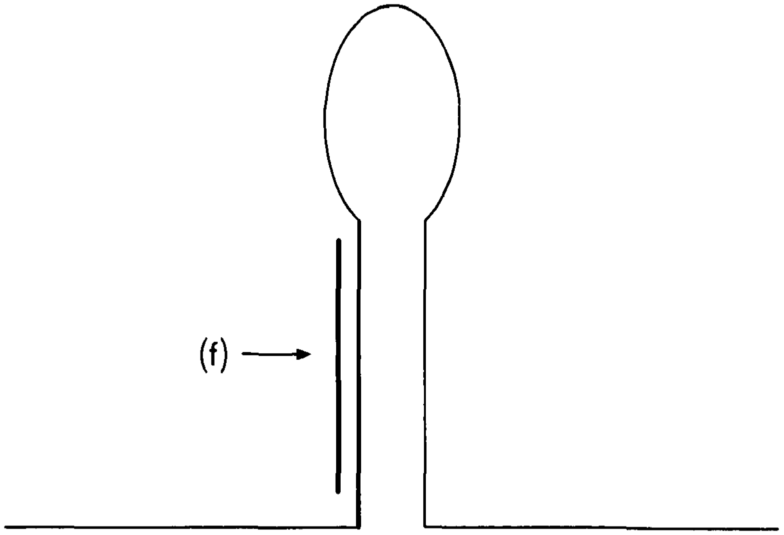
Figure 2:
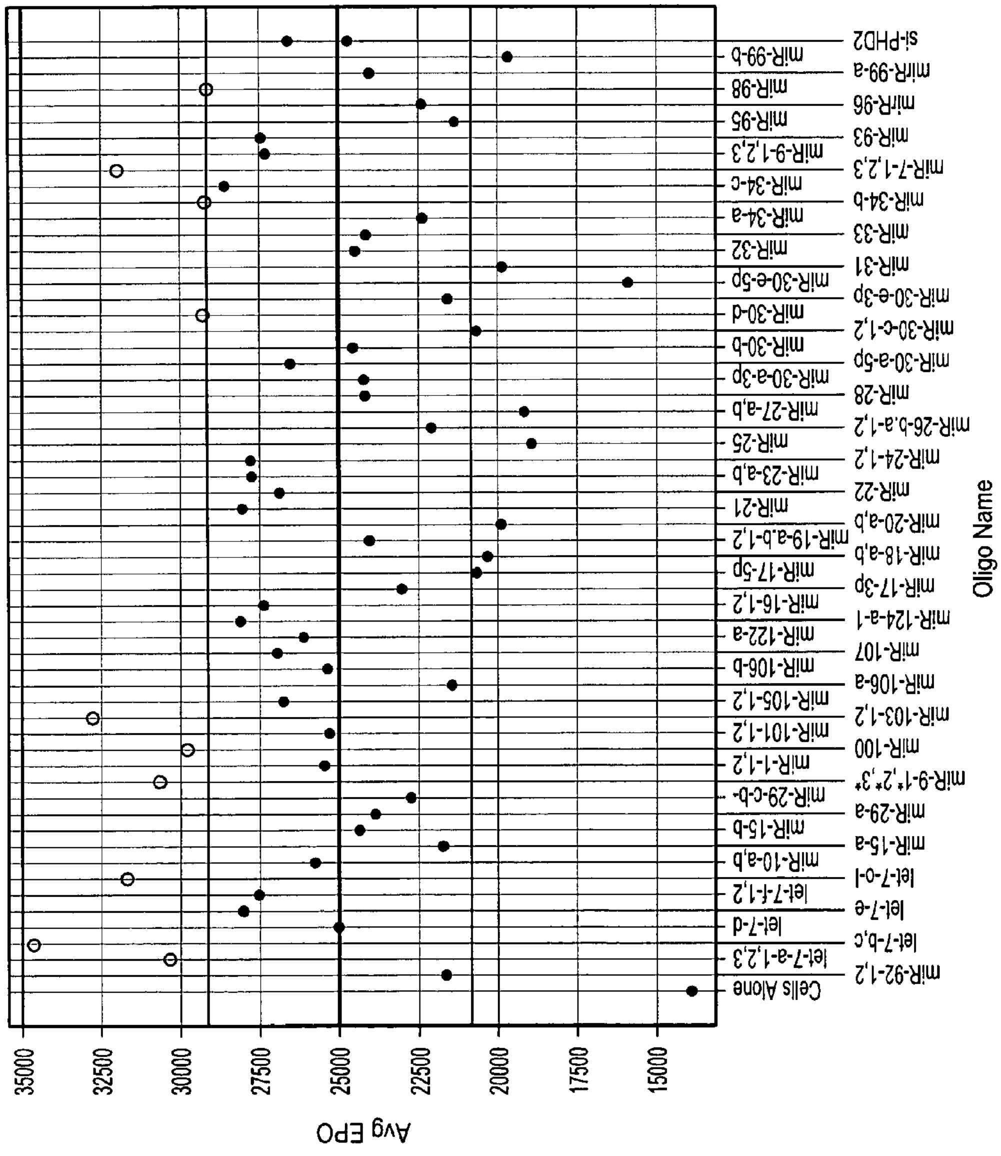
FIGS. 2-6 show data collected in a screen of nucleic acids at a concentration of 400 nM in Kelly cells targeting the noted microRNAs.
Figure 3:
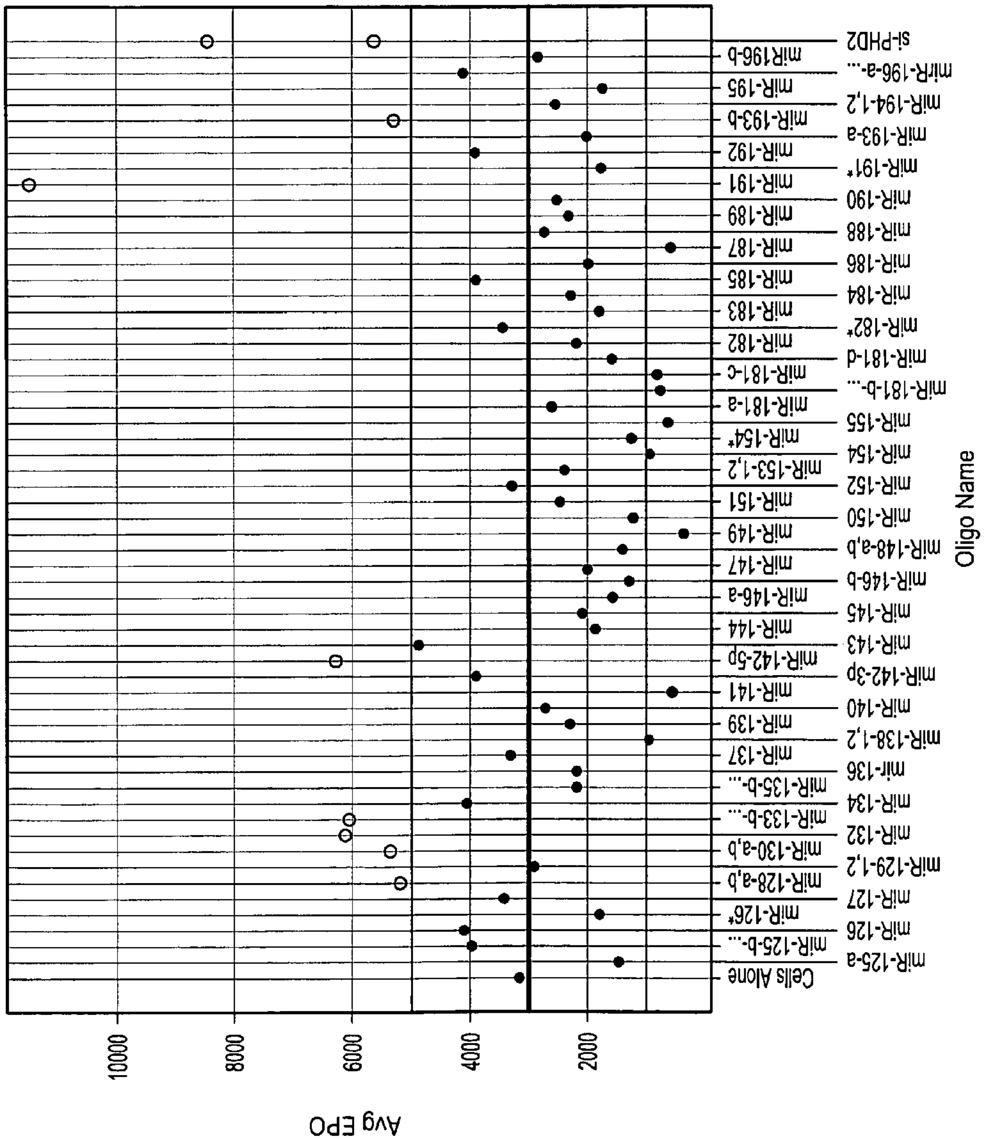
Figure 4:
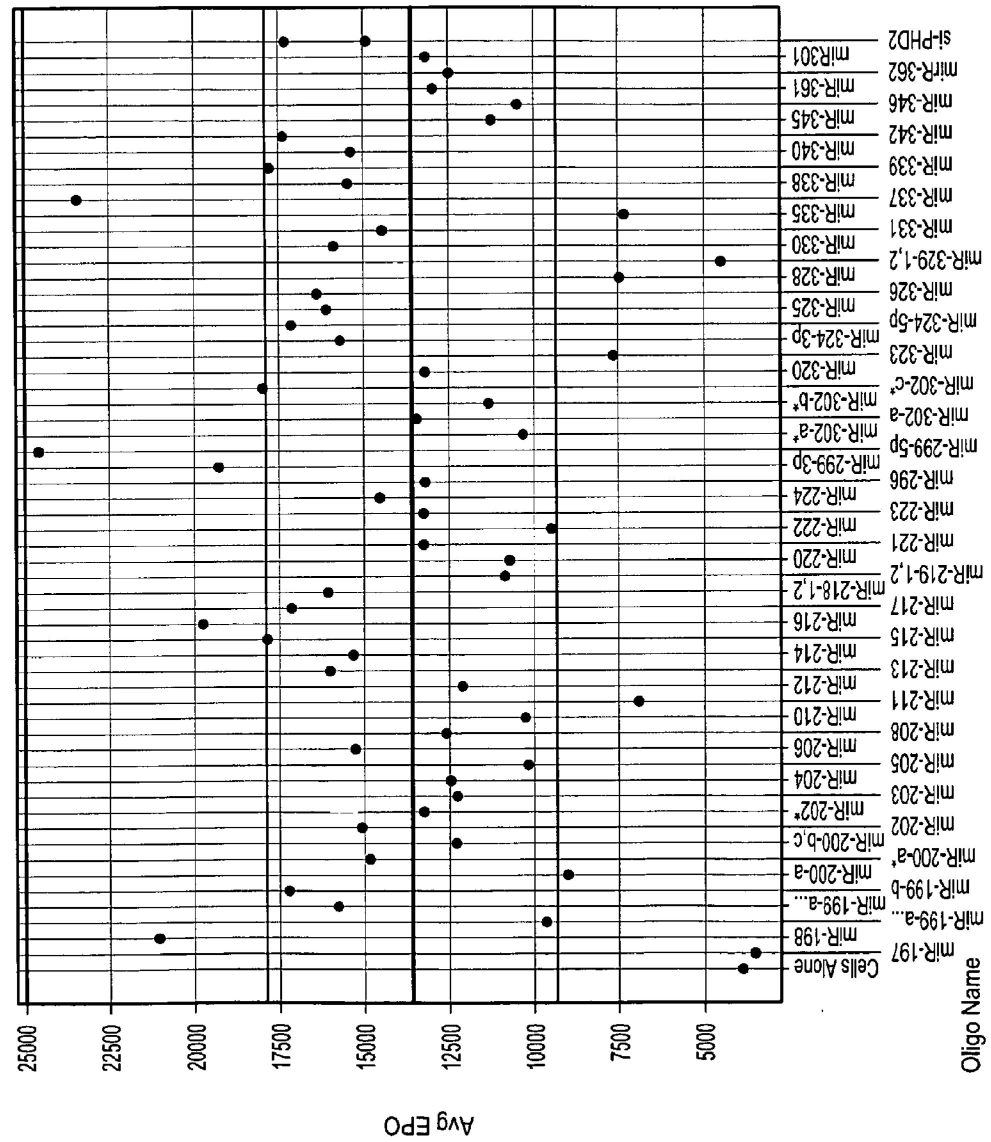
Figure 5:
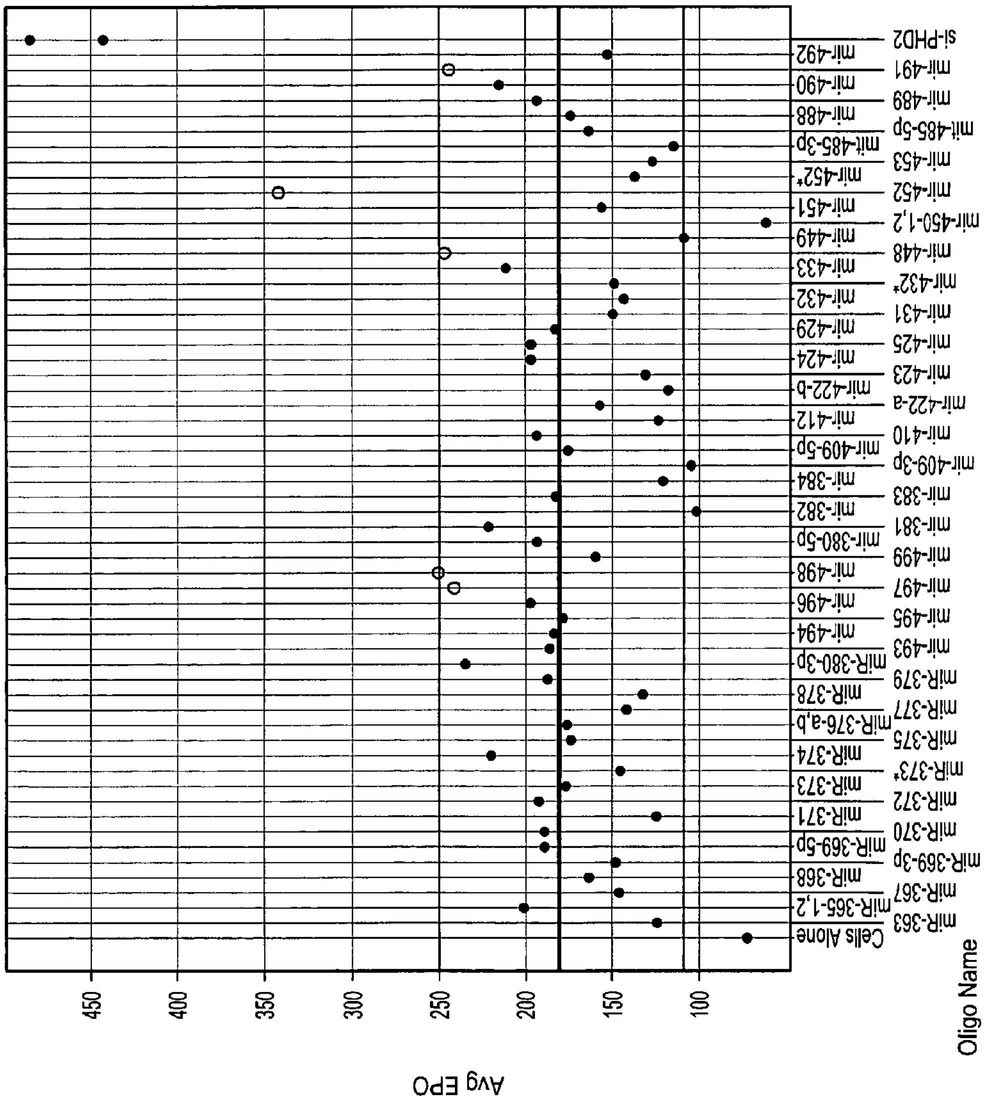
Figure 6:
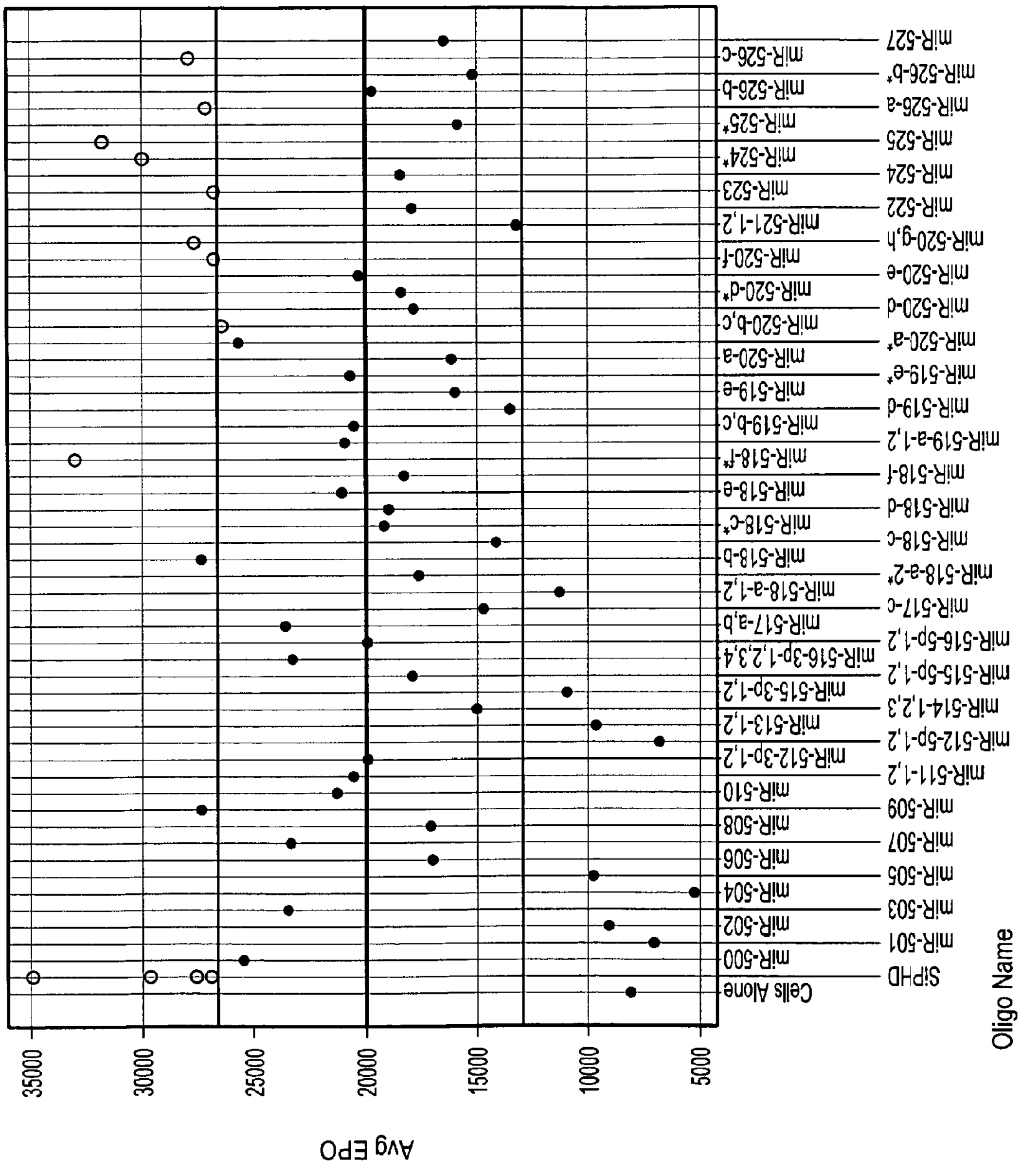

For example, without being bound by any particular theory, a nucleic acid may be designed to block the processing of pre-miRNAs by Dicer by targeting part of the loop and part of the stem of a pre-miRNA (see e.g. nucleic acids (a) and (b) in FIG. 1A). In other embodiments, nucleic acids are designed to block the processing of pri-miRNAs by Drosha by targeting part of the stem and part of either part of the single stranded RNA at the base of the stem (see e.g. nucleic acids (c) and (d) in FIG. 1A). Without being bound by any particular theory, the export of pre-miRNA to the cytoplasm by Exportin may be blocked by targeting pre-miRNA. In some embodiments, a nucleic acid may be designed to block Drosha processing by targeting two discontinuous extensions of the base of the stem in a pri-miRNA sequence (see e.g. nucleic acids (e) in FIG. 1A). In another embodiment, a nucleic acid may be designed to target the stem portion of an miRNA precursor (see e.g. nucleic acid (f) in FIG. 1B). Thus, when a nucleic acid is referred to as being able to hybridize to a miRNA it is meant that the nucleic acid can hybridize, for example, in any of the configurations shown in FIGS. 1A and 1B.

Any portions of the miRNA participating in mRNA binding may be targeted. In some embodiments, the first 6, 7, or 8 nucleotides from the 5' end of the miRNA may be targeted. Such locations on the target miRNA or precursor thereof to which nucleic acid hybridizes may be referred to as a "suitable target segment." As used herein, the term "suitable target segment" is defined as at least a 6, 7 or 8-nucleotide portion of a target region to which a nucleic acid is targeted. Once one or more target regions have been identified, nucleic acids are designed to be sufficiently complementary to the target, i.e., hybridize sufficiently well and with sufficient specificity, to give the desired effect (e.g. increasing the expression and/or secretion of EPO).

In some embodiments, the one or more anti-miRNA nucleic acid may be targeted to a first miRNA target and one or more additional anti-miRNA nucleic acids targeted to a second miRNA target. Alternatively, compositions may contain two or more anti-miRNA nucleic acids targeted to different regions, segments or sites of the same miRNA target. Two or more combined anti-miRNA compounds may be used together or sequentially.

In other embodiments, the nucleic acid is designed to target, at least in part, the seed region of the miRNA. Thus, in this embodiment, the target region includes at least a portion or the entire seed region of the miRNA. The term "seed region," as used herein, refers to nucleotides at the 5' end of the miRNA sequence that are typically common to an miRNA family. Examples of seed regions for certain miRNAs are set forth in Table 3 below (see underlined portion). In certain embodiments, the seed region includes 3, 4, 5, 6, 7, 8, 9, or 10 consecutive nucleotides within the miRNA sequence. Typically, the seed region of the miRNA is 6, 7, or 8 consecutive nucleotides within the miRNA sequence. For example, the seed region of the miRNA sequence may be nucleotides 1 through 7, 1 through 8, 2 through 7, 2 through 8, 1 through 9, 1 through 10, 2 through 9, 2 through 10, 3 through 10, or 4 through 12 from the 5' end of the miRNA sequence. In some embodiments, the seed region of the miRNA sequence may advantageously be inclusively defined as nucleotides 1 through 7, 1 through 8, 2 through 7, or 2 through 8 from the 5' end of the miRNA sequence. See Table 3 which depicts exemplary seed regions (underlined) for the target miRNA sequences of SEQ ID NOs:39-77.

The methods described herein (e.g. of increasing the expression and/or secretion of EPO and treating disease states such as anemia, hemophilia and sickle cell disease) include the use of a nucleic acid that is hybridizable to an RNA molecule, is antisense to an RNA molecule, is substantially complimentary to an RNA molecule, and/or has a sequence with at least 70% sequence identity to a 6 or more nucleobase (or nucleotide) sequence (e.g. contiguous sequence) of one of SEQ ID NOs: 1-38 (also referred to herein as "anti-miRNA nucleic acid sequences"). See Table 2 for the complete sequences of SEQ ID NOs: 1-38. The RNA molecule may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO:

47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof In certain embodiments, the nucleic acid comprises or consists of a sequence having at least 70% sequence identity to a 6, 7, 8, 9, 10, 11, 12, 13, 14, 15, 16, 17, 18, 19, 20, or 21 nucleobase sequence of one of SEQ ID NOs: 1-38. These nucleic acids are capable of increasing expression and/or secretion of EPO in a cell relative to the absence of the nucleic acids. Appropriate assays for testing the ability of nucleic acids are provided below in Sections VI and VIII. The "nucleobase sequence" refers to consecutive nucleobases within the relevant SEQ ID NO. For example, the nucleic acid may comprise or consist of a sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with any one of SEQ ID NOs: 1-38, or to a 6, 7, 8, 9, 10, 11, 12, 13, 14, 15, 16, 17, 18, 19, or 20 nucleobase sequence of one of SEQ ID NOs: 1-38. In some embodiments, the nucleic acid comprises or consists of a sequence having 100% sequence identity with an anti-miRNA sequence (e.g. one of SEQ ID NOs 1-38).

In some embodiments, the nucleic acid is at least 12 nucleobases in length. In other embodiments, the nucleic acid is at least 15 nucleobases in length. The nucleic acid may also be less than 22 nucleobases in length. Thus, in some embodiments, the nucleic acid is from 7 to 21 nucleobases in length. In other embodiments, the nucleic acid is from 8 to 21, 9 to 21, 10 to 21, 11 to 21, 12 to 21, 13 to 21, 14 to 21, 15 to 21, 16 to 21, 17 to 21, or 18 to 21 nucleobases in length. In some instances, the nucleic acid is 7, 8, 9, 10, 11, 12, 13, 14, 15, 16, 17, 18, 19, 20, or 21 nucleobases in length.

Certain correlations between targeted RNA molecules and the respective nucleic acid anti-miRNA sequences are set forth in Table 2. Thus, as illustrated in Table 2, in some embodiments, the RNA molecule is an miRNA comprising a sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof, (and precursors thereof), and the nucleic acid comprises or consists of a sequence having at least 70% sequence identity to a nucleobase sequence of or within one of SEQ ID NO:1-38, respectively. One skilled in the art will recognize that SEQ ID NO:2 targets both miR-103-1,2 (SEQ ID NO: 40) and miR-107 (SEQ ID NO: 41). Thus, the number of SEQ ID NOs are one less than the number of corresponding miRNAs.

In other embodiments of the correlations set forth in Table 2, the nucleic acid comprises or consists of a sequence 7, 8, 9, 10, 11, 12, 13, 14, 15, 16, 17, 18, 19, 20, or 21 nucleobases, and having at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity with the respective nucleic acid SEQ ID NOs:1-38. In still other embodiments of the correlations set forth in Table 2, the RNA molecule is an miRNA selected from one of the embodiments of miRNA listings set forth above. For example, in another embodiment of the correlations set forth in Table 2, the RNA molecule may comprise an miRNA selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51) and precursors thereof, and the respective nucleic acid has the appropriate number of nucleobases and the appropriate sequence identity as set forth in the previous sentence.

The nucleic acid may include a sequence that differs by no more than 8 nucleobases (or nucleotides) from any one of SEQ ID NOs: 1-38. In other embodiments, the nucleic acid may include a sequence that differs by no more than 5, 6, or 7 nucleobases (or nucleotides) from any one of SEQ ID NOs: 1-38. In other embodiments, the nucleic acid may include a sequence that differs by no more than 1, 2, 3 or 4 nucleobases (or nucleotides) from any one of SEQ ID NOs:1-38.

In some embodiments, the nucleic acid is selected to minimize VEGF expression while increasing EPO expression and/or secretion. For example, in certain embodiments, the anti-miRNA nucleic acid may comprise the nucleic acid sequence of SEQ ID NO: 4, which hybridizes to and antagonizes the activity of miR-337 (SEQ ID NO:43), SEQ ID NO: 8, which hybridizes to and antagonizes the activity of miR-198 (SEQ ID NO: 47), SEQ ID NO: 9, which hybridizes to and antagonizes the activity of miR-299-3p (SEQ ID NO: 48), SEQ ID NO: 10, which hybridizes to and antagonizes the activity of miR-299-5p (SEQ ID NO: 49), SEQ ID NO: 11, which hybridizes to and antagonizes the activity of miR-498 (SEQ ID NO: 50), and SEQ ID NO: 12, which hybridizes to and antagonizes the activity of miR-518-f* (SEQ ID NO: 51), or precursors thereof. Thus, the respective corresponding nucleic acids may be SEQ ID NOs: 4, and SEQ ID NOs 8-12, where the respective nucleic acid has the appropriate number of nucleobases and the appropriate sequence identity as set forth above.

As stated above, the nucleic acid may hybridize under stringent conditions to the RNA molecule. In some embodiment, the nucleic acid hybridizes under low stringency hybridization conditions to the RNA molecule. In other embodiments, the nucleic acid hybridizes under moderately stringent hybridization conditions to the RNA molecule. In other embodiments, the nucleic acid hybridizes under highly stringent hybridization conditions to the RNA molecule.

In some embodiments, the nucleic acid is substantially complementary to the miRNA or miRNA precursor. The nucleic acid may be at least 50%, at least 60%, at least 70%, at least 75%, at least 80%, or at least 85% sequence complementarity to a target region (e.g. seed region) within the miRNA or miRNA precursor. In other embodiments, the nucleic acid includes at least 90%, at least 91%, at least 92%, at least 93%, or at least 94%, sequence complementarity to a target region (e.g. seed region) within the miRNA or miRNA precursor. In other embodiments, the nucleic acid includes at least 95%, at least 96%, at least 97%, at least 98%, or at least 99% sequence complementarity to a target region (e.g. seed region) within the miRNA or miRNA precursor. For example, a nucleic acid in which 18 of 20 of its nucleobases are complementary to a target sequence (e.g. seed region) would represent 90 percent complementarity. Where a nucleic acid is substantially complementary to a miRNA or precursor, the remaining non-complementary nucleobases may be clustered or interspersed with complementary nucleobases and need not be contiguous to each other or to complementary nucleobases. Thus, a nucleic acid which is 22 nucleobases in length having 6 (six) non-complementary nucleobases which are flanked by two regions of complete complementarity with the target miRNA or miRNA precursor would have 72.7% overall complementarity with the miRNA or miRNA precursor. Percent complementarity of a nucleic acid with a region of an miRNA or miRNA precursor can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). In some embodiments, the nucleic acid is perfectly complementary to the miRNA or miRNA precursor.

Any appropriate method for introducing the nucleic acid into the cell may be employed. Examples of suitable methods include, for example, cell transfection methods such as chemical, biological or mechanical means. Recognized methods include electroporation, use of a virus vector, lipofection, gene guns, and microinjection.

The method may be practiced with any appropriate cell, such as a plant or animal cell. In some embodiments, the cell is a mammalian cell, such as a human cell. The cell may also be a HepG2 or Kelly cell. Thus, in certain embodiments, the methods of introducing the nucleic acid into the cell are performed in vitro. Once into the cell, the nucleic acid increases the expression and/or secretion of EPO, in situ.

IV. Methods of Treating a Subject

A variety of methods for treating anemia, hemophilia, or sickle cell disease in a subject in need thereof, enhancing erythropoiesis, and increasing EPO levels in a subject are also provided. The methods include administering to the subject an effective amount of a anti-miRNA nucleic acid that is hybridizable to an RNA molecule, is antisense to the RNA molecule, is substantially complimentary to the RNA molecule, and/or has a sequence with at least 70%, at least 75%, at least 80%, at least 85% at least 90%, at least 91%, at least 92%, at least 93%, at least 94%, at least 95%, at least 96%, at least 97%, at least 98%, or at least 99% sequence identity to a 6 or more nucleobase (or nucleotide) sequence of one of SEQ ID NOs: 1-38. In these methods, the RNA molecules that are targeted and the nucleic acids used to hybridize to the targeted RNA molecule are the same as those described above. Thus, the same sequence, length and other characteristics of the nucleic acids described in Section III apply equally to the methods for treating anemia, hemophilia, or sickle cell disease, enhancing erythropoiesis, and increasing EPO levels in a subject.

An effective amount is an amount effective to achieve a stated purpose, such as to treat anemia, hemophilia, or sickle cell disease, enhance erythropoiesis, and increase EPO levels. In some embodiments, and effective amount is a therapeutically effective amount or a prophylactically effective amount. A "therapeutically effective amount" is an amount sufficient to remedy a disease state (e.g. anemia) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount that, when administered to a subject, will have the intended prophylactic effect, e.g., preventing or delaying the onset (or reoccurrence) of a particular disease state, or reducing the likelihood of the onset (or reoccurrence) of a particular disease state or a particular symptom of a disease. The full prophylactic effect does not necessarily occur by administration of one dose, and may occur only after administration of a series of doses. Thus, a prophylactically effective amount may be administered in one or more administrations.

The nucleic acid sequences of SEQ ID NOs: 1-38 hybridize to the target miRNA sequences of SEQ ID NOs: 39-77 in accordance with Table 3. Thus, nucleic acid SEQ ID NO:1 hybridizes to miR-100 (SEQ ID NO: 39), nucleic acid SEQ ID NO:2 hybridizes to miR-103-1,2 (SEQ ID NO: 40), and so on (as variously described herein).

The embodiments of the anti-miRNA nucleic acid molecules that hybridize to the RNA molecules discussed in the section above are equally applicable to the methods of treating anemia, hemophilia, or sickle cell disease. For example, in some embodiments, the RNA molecule may comprise an miRNA selected from miR-100 (SEQ ID NO:39), miR-103-1,2 (SEQ ID NO:40), miR-107 (SEQ ID NO:41), miR-191 (SEQ ID NO:42), miR-337 (SEQ ID NO:43), miR-520-f (SEQ ID NO:44), miR-520-g,h (SEQ ID NO:45), miR-524* (SEQ ID NO:46), miR-198 (SEQ ID NO:47), miR-299-3p (SEQ ID NO:48), miR-299-5p (SEQ ID NO:49), miR-498 (SEQ ID NO:50), miR-518-f* (SEQ ID NO:51) and precursors thereof. In other embodiments, the RNA molecule may comprise an miRNA selected from miR-100 (SEQ ID NO:39), miR-103-1,2 (SEQ ID NO:40), miR-107 (SEQ ID NO:41), miR-191 (SEQ ID NO:42), miR-337 (SEQ ID NO:43), miR-520-f (SEQ ID NO:44), miR-520-g,h (SEQ ID NO:45), miR-524* (SEQ ID NO:46) and precursors thereof. The RNA molecule may also comprise miR-100 (SEQ ID NO:39), miR-103-1,2 (SEQ ID NO:40), miR-107 (SEQ ID NO:41), miR-337 (SEQ ID NO:43), miR-524* (SEQ ID NO:46), and precursors thereof. The RNA molecule may also comprise miR-103-1,2 (SEQ ID NO:40), miR-107 (SEQ ID NO:41), miR-524* (SEQ ID NO:46) and precursors thereof. The RNA molecule may also comprise miR-100 (SEQ ID NO:39), miR-103-1,2 (SEQ ID NO:40), miR-107 (SEQ ID NO:41), miR-191 (SEQ ID NO:42), miR-337 (SEQ ID NO:43), miR-524* (SEQ ID NO:46) and precursors thereof. The RNA molecule may also comprise miR-100 (SEQ ID NO:39), miR-103-1,2 (SEQ ID NO:40), miR-107 (SEQ ID NO:41) and precursors thereof. The RNA molecule may also comprise miR-337 (SEQ ID NO:43), miR-198 (SEQ ID NO:47), miR-299-3p (SEQ ID NO:48), miR-299-5p (SEQ ID NO:49), miR-498 (SEQ ID NO:50), miR-518-f* (SEQ ID NO:51) and precursors thereof. The RNA molecule may also comprise miR-337 (SEQ ID NO:43), miR-299-5p (SEQ ID NO:49) and precursors thereof. The RNA molecule may also miR-337 (SEQ ID NO:43) and precursors thereof.

The nucleic acid is hybridizable to the RNA molecule, is antisense to the RNA molecule, is substantially complimentary to the RNA molecule, and/or has a sequence with at least 70% sequence identity to a 6 or more nucleobase (or nucleotide) sequence of one of SEQ ID NOs: 1-38. See Table 2 for the sequences of SEQ ID NOs: 1-38. As with the RNA molecule embodiments, the embodiments of the nucleic acid discussed in Section III above are equally applicable to the methods of treating anemia, hemophilia, or sickle cell disease, increasing EPO levels, and enhancing erythropoiesis in a subject. Thus, for example, the nucleic acid may comprise or consist of a sequence having at least 75%, at least 80% at least 85%, at least 90%, at least 91%, at least 92%, at least 93%, at least 94%, at least 95%, at least 96%, at least 97%, at least 98%, at least 99% or 100% sequence identity with an 6, 7, 8, 9, 10, 11, 12, 13, 14, 15, 16, 17, 18, 19, or 21 nucleobase sequence within any one of SEQ ID NOs: 1-38. Alternatively, the nucleic acid may comprise or consist of a sequence that differs by no more than 8 nucleobases (or nucleotides) from any one of SEQ ID NOs:1-38. In other embodiments, the nucleic acid may include a sequence that differs by no more than 5, 6, or 7 nucleobases (or nucleotides) from any one of SEQ ID NOs:1-38. In other embodiments, the nucleic acid may include a sequence that differs by no more than 1, 2, 3 or 4 nucleobases (or nucleotides) from any one of SEQ ID NOs:1-38.

The nucleic acid can be administered by any suitable method that is effective in the treatment of anemia, hemophilia, and sickle cell disease. Thus, for instance, administration can be oral, rectal, topical, parenteral or intravenous administration or by injection. The method of applying an effective amount also varies depending on the disorder or disease being treated. Parenteral treatment by intravenous, subcutaneous, or intramuscular application of the nucleic acid, formulated with an appropriate carrier, additional compound or compounds or diluent to facilitate application are suitable alternatives in administering the nucleic acid to a subject.

The nucleic acids may be combined (e.g. co-administered) with other active agents for use in combination therapies. For example, in some embodiments, the nucleic acid is combined with another anemia, hemophilia, and sickle cell disease therapies. For example, other therapies that may be used in combination with the nucleic acids described herein include co-administration of the nucleic acids with appropriate agents such as iron, drugs used in the treatment of HIV (e.g. AZT), anemia, cancer (e.g. cisplatin), hypertension, and thrombotic events.

One skilled in the art will recognize that the efficacy of the nucleic acids can be ascertained through routine screening using known cell lines both in vitro and in vivo. Cell lines are available from American Tissue Type Culture or other laboratories.

The methods and compositions described herein are suitable for use in erythropoietin therapy procedures practiced on mammals, including humans, to develop any or all of the effects here fore attributed to EPO, e.g., stimulation of reticulocyte response, development of ferrokinetic effects (such as plasma iron turnover effects and marrow transit time effects), erythrocyte mass changes, stimulation of hemoglobin C synthesis (see, Eschbach, et al., supra), tissue protective effects (e.g. cardio protection), and increasing hematocrit levels in mammals. Included within the class of subjects treatable with products of the invention are patients generally requiring blood transfusions and including trauma victims, surgical patients, renal disease patients including dialysis patients, and patients with a variety of blood composition affecting disorders, such as hemophilia, sickle cell disease, physiologic anemias, and the like. The minimization of the need for transfusion therapy through use of EPO therapy can be expected to result in reduced transmission of infectious agents. The methods and compositions are also useful in the enhancement of oxygen carrying capacity of individuals encountering hypoxic environmental conditions and possibly in providing beneficial cardiovascular effects.

The methods and compositions may thus be used to stimulate red blood cell production and correct depressed red cell levels. Most commonly, red cell levels are decreased due to anemia. Among the conditions treatable by the present invention include anemia associated with a decline or loss of kidney function (e.g. chronic renal failure, acute renal failure, and end-stage renal disease), anemia associated with myelosuppressive therapy, such as chemotherapeutic or anti-viral drugs (such as AZT), anemia associated with the progression of non-myeloid cancers, and anemia associated with viral infections (such as HIV). Also treatable are conditions which may lead to anemia in an otherwise healthy individual, such as an anticipated loss of blood during surgery. The nucleic acids can also be used to treat anemic patients scheduled to undergo elective, noncardiac, nonvascular surgery to reduce the need for allogeneic blood transfusions. In general, any condition treatable with rHuEPO and/or NESP may also be treated using methods and composition described herein.

V. Nucleic Acids and General Nucleic Acid Syntheses

A. Types of Nucleic Acids

The nucleic acid may be modified to increase stability of the nucleic acids toward nucleases, to increase hybridization stability, or to increase inhibition of miRNA or miRNA precursor function. In some embodiments, the nucleic acid includes modifications to the standard phosphodiester linkages found in natural or unmodified nucleic acids. Modified nucleic acid backbones (internucleotide linkages) containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkyiphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. The preparation of the above phosphorus-containing linkages is discussed in greater detail below and, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference. In some embodiments, the nucleic acid includes one or more modified internucleotide or internucleoside linkages selected from phosphoroamidate, phosphorothiate, phosphorodithioate, boranophosphate, alkylphosphonate, and methylinemethylimino. For further description of methylinemethylimino internucleoside linkages, see U.S. Pat. Nos. 5,378,825, 5,386, 023, 5,489,677, 5,602,240, and 5,610,289, each of which is herein incorporated by reference. Appropriate mixed backbone nucleic acid linkages, with standard phosphodiester linkages or with one or more different modified internucleotide or internucleoside linkages, are useful in the methods described herein.

The nucleic acid may also include a modified nucleic acid unit selected from a locked nucleic acid unit, 2'-O-alkyl ribonucleic acid units (including 2'-O-methyl ribonucleic acid unit and 2'O-methoxy-ethyl ribonucleic acid unit), 2'alkyl ribonucleic acid unit, 2'amine ribonucleic acid unit, peptide nucleic acid unit, 2'fluoro-ribo nucleic acid unit, morpholino nucleic acid unit, cyclohexane nucleic acid unit, or a tricyclonucleic acid unit. For further information regarding modified nucleic acid units, see U.S. App. No. 2005/0182005, which is herein incorporated by reference. In some embodiments, the nucleic acid is a locked nucleic acid (i.e. a nucleic acid containing at least 90%, 91%, 92%, 93%, 94%, 95%, 96%, 97%, 98%, 99%, or 100% locked nucleic acid units), a 2'-O-methyl ribonucleic acid (i.e. a nucleic acid containing at least 90%, 91%, 92%, 93%, 94%, 95%, 96%, 97%, 98%, 99%, or 100% 2'-O-methyl ribonucleic acid units), or a 2'-O-methoxy-ehtyl ribonucleic acid (i.e. a nucleic acid containing at least 90%, 91%, 92%, 93%, 94%, 95%, 96%, 97%, 98%, 99%, or 100% a 2'-O-methoxy-ehtyl ribonucleic acid units). In some embodiments, the nucleic acid is a locked nucleic acid, a 2'-O-methyl ribonucleic acid or a mixed nucleic acid-locked nucleic acid (i.e. a nucleic acid containing at least 50% locked nucleic acid units, with the remaining units being ribonucleic acid units or deoxyribonucleic acid units). In still other embodiments, the nucleic acid is a locked nucleic acid or a mixed nucleic acid-locked nucleic acid In some embodiments, a nucleic acid is provided having at least 80%, 85%, or 90% locked nucleic acid units. In some related embodiments, the remaining units are ribonucleic acid units or deoxyribonucleic acid units, typically ribonucleic acid units. In other embodiments, the nucleic acid includes at least 80%, 85%, 86%, 87%, 88%, 89%, 90%, 91%, 92%, 93%, 94%, 95%, 96%, 97%, 98%, or 99% locked nucleic acid units. The nucleic acid is hybridizable to an RNA molecule, is antisense to an RNA molecule, is substantially complimentary to an RNA molecule, and/or has a sequence with at least 70% sequence identity to a 6 or more nucleobase (or nucleotide) sequence of one of SEQ ID NOs: 1-38. The RNA molecule may comprise an miRNA sequence selected from miR-100 (SEQ ID NO: 39), miR-103-1,2 (SEQ ID NO: 40), miR-107 (SEQ ID NO: 41), miR-191 (SEQ ID NO: 42), miR-337 (SEQ ID NO: 43), miR-520-f (SEQ ID NO: 44), miR-520-g,h (SEQ ID NO: 45), miR-524* (SEQ ID NO: 46), miR-198 (SEQ ID NO: 47), miR-299-3p (SEQ ID NO: 48), miR-299-5p (SEQ ID NO: 49), miR-498 (SEQ ID NO: 50), miR-518-f* (SEQ ID NO: 51), let-7-a-1,2,3 (SEQ ID NO: 52), let-7-b,c (SEQ ID NO: 53), let-7-g-I (SEQ ID NO: 54), miR-7-1,2,3 (SEQ ID NO: 55), miR-9*-1,2,3 (SEQ ID NO: 56), miR-30-d (SEQ ID NO: 57), miR-34-b (SEQ ID NO: 58), miR-98 (SEQ ID NO: 59), miR-128-a,b (SEQ ID NO: 60), miR-132 (SEQ ID NO: 61), miR-133-a,b,1,2 (SEQ ID NO: 62), miR-216 (SEQ ID NO: 63), miR-448 (SEQ ID NO: 64), miR-452 (SEQ ID NO: 65), miR-491 (SEQ ID NO: 66), miR-497 (SEQ ID NO: 67), miR-520-b,c (SEQ ID NO: 68), miR-130-a,b (SEQ ID NO: 69), miR-142-5p (SEQ ID NO: 70), miR-193-b (SEQ ID NO: 71), miR-509 (SEQ ID NO: 72), miR-523 (SEQ ID NO: 73), miR-525 (SEQ ID NO: 74), miR-526-a (SEQ ID NO: 75), miR-526-c (SEQ ID NO: 76), miR-518-b (SEQ ID NO: 77), and precursors thereof. Where a nucleic acid includes a defined percentage of locked nucleic acid units, the percentage is the number of locked nucleic acid units divided by the total number of nucleic acid units multiplied by 100%. In some embodiments, all of the nucleic acid units within the nucleic acid are locked nucleic acid units with the exception of 1, 2, 3, 4 or 5 nucleic acid units (e.g., nucleotides). In some embodiments, the internucleotide linkages are phosphodiester linkages or phosphorothioate linkages. Any nucleic acid units that are not locked nucleic acid units may be selected from ribonucleic acid units, deoxyribonucleic acid units, and 2'-O-methyl nucleic acid units. The nucleic acid may be any appropriate length as described in Section III above (e.g. 7, 8, 9, 10, 11, 12, 13, 14, 15, 16, 17, 18, 19, 20, or 21 nucleobases in length). In some embodiments, the nucleic acid has at least 75%, at least 80%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 1-38, or to a 6, 7, 8, 9, 10, 11, 12, 13, 14, 15, 16, 17, 18, 19, or 20 nucleobase sequence of one of SEQ ID NOs: 1-38.

The nucleic acids can have one or more moieties bound or conjugated, which facilitates the active or passive transport, localization, or compartmentalization of the nucleic acid. Cellular localization includes, but is not limited to, localization to within the nucleus, the nucleolus, or the cytoplasm. Compartmentalization includes, but is not limited to, any directed movement of the nucleic acids compounds to a cellular compartment including the nucleus, nucleolus, mitochondrion, or imbedding into a cellular membrane.

One substitution that can be appended to the nucleic acids involves the linkage of one or more moieties or conjugates which enhance the activity, cellular distribution or cellular uptake of the resulting nucleic acids. In one embodiment such modified nucleic acids are prepared by covalently attaching conjugate groups to functional groups such as hydroxyl or amino groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, carbohydrates, lipids, phospholipids, biotin, phenazine, folate, phenanthridine, anthraquinone, acridine, fluoresceins, rhodamines, coumarins, and dyes. Groups that enhance the pharmacodynamic properties include groups that improve oligomer uptake, enhance oligomer resistance to degradation, and/or strengthen hybridization with RNA. Groups that enhance the pharmacokinetic properties include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecanediol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glyc-ero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

The nucleic acids may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Nucleic acid-drug conjugates and their preparation are described in U.S. patent application Ser. No. 09/334,130 (filed Jun. 15, 1999) which is incorporated herein by reference in its entirety.

Representative U.S. patents that teach the preparation of such nucleic acid conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference for all purposes.

Nucleic acids can also be modified to have one or more stabilizing groups that are generally attached to one or both termini of nucleic acids to enhance properties such as for example nuclease stability. Included in stabilizing groups are cap structures. By "cap structure or terminal cap moiety" is meant chemical modifications, which have been incorporated at either terminus of nucleic acids (see for example Wincott et al., WO 97/26270, incorporated by reference herein). These terminal modifications protect the nucleic acids having terminal nucleic acid molecules from exonuclease degradation, and can help in delivery and/or localization within a cell. The cap can be present at the 5'-terminus (5'-cap) or at the 3'-terminus (3'-cap) or can be present on both termini. For double-stranded nucleic acids, the cap may be present at either or both termini of either strand. In non-limiting examples, the 5'-cap includes inverted abasic residue (moiety), 4',5'-methylene nucleotide; 1-(beta-D-erythrofuranosyl)nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (see Wincott et al., International PCT publication No. WO 97/26270, incorporated by reference herein).

Useful 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein). Further 3' and 5'-stabilizing groups that can be used to cap one or both ends of a nucleic acid to impart nuclease stability include those disclosed in WO 03/004602 published on Jan. 16, 2003.

B. General Nucleic Acid Syntheses

Oligomerization of modified and unmodified nucleosides is performed according to literature procedures for DNA like compounds (see, e.g., Protocols for Oligonucleotides and Analogs, Ed. Agrawal (1993), Humana Press) and/or RNA like compounds (see, e.g., Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. In addition, some examples of protocols for the synthesis of nucleic acids are illustrated below.

RNA can be synthesized by methods disclosed herein or purchased from various RNA synthesis companies (e.g. Dharmacon Research Inc., (Lafayette, Colo.)).

Regardless of the particular protocol used, the nucleic acids used herein may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The following compounds, including amidites and their intermediates can be prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-$N_4$-benzoyl-5-methylcytidine penultimate intermediate for 5-methyl dC amidite, (5'-O-(4,4'-Dimethoxytriphenylmethyl)-2'-deoxy-$N_4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N_4$-benzoyl-5-methyl-cytidine penultimate intermediate, (5'-O-(4,4'-Dimethoxytriphenylmethyl)-2'-O-(2-methoxyethyl)-$N_4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N_6$-benzoyladenosin-3'-O-yl)-2-cyanoethyl-N,N-diisopropylphosphoramidite (MOE A amidite), (5'-O-(4,4'-Dimethoxytriphenylmethyl)-2'-O-(2-methoxyethyl)-$N_4$-isobutyrylguanosin-3'-O-yl)-2-cyanoethyl-N,N-diisopropylphosphoramidite (MOE G amidite), 2'-O-

(Aminooxyethyl)nucleoside amidites and 2'-O-(dimethylaminooxyethyl)nucleoside amidites, 2'-(Dimethylaminooxyethoxy)nucleoside amidites, 5'-O-tert-Butyldiphenylsilyl-$O_2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O-(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy)nucleoside amidites, $N_2$-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy(2'-DMAEOE)nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl-))-5-methyl uridine-3'-O-(cyanoethyl-N,N-diisopropyl)phosphoramidite.

Unsubstituted and substituted phosphodiester (P═O) nucleic acids can be synthesized on an automated nucleic acid synthesizer (Applied Biosystems model 394) using standard phosphoramidite chemistry with oxidation by iodine. Generally, nucleic acids can be cleaved from solid support (e.g. a controlled pore glass column) and deblocked in concentrated ammonium hydroxide, then recovered by precipitation using $NH_4OAc$ with ethanol. Synthesized nucleic acids may be analyzed by electrospray mass spectroscopy (molecular weight determination) and by capillary gel electrophoresis.

Phosphorothioates (P═S) can be synthesized similar to phosphodiester nucleic acids with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the solid support and deblocking in concentrated ammonium hydroxide at the appropriate temperature, the nucleic acids may be recovered by precipitating with ethanol from a 1 M $NH_4OAc$ solution. Phosphinate nucleic acids can be prepared as described in U.S. Pat. No. 5,508,270, herein incorporated by reference.

Alkyl phosphonate nucleic acids can be prepared as described in U.S. Pat. No. 4,469,863, herein incorporated by reference.

3'-Deoxy-3'-methylene phosphonate nucleic acids can be prepared as described in U.S. Pat. No. 5,610,289 or 5,625,050, herein incorporated by reference.

Phosphoramidite nucleic acids can be prepared as described in U.S. Pat. No. 5,256,775 or U.S. Pat. No. 5,366,878, herein incorporated by reference.

Alkylphosphonothioate nucleic acids can be prepared as described in published PCT applications PCT/US94/00902 and PCT/US93/06976 (published as WO 94/17093 and WO 94/02499, respectively), herein incorporated by reference.

3'-Deoxy-3'-amino phosphoramidate nucleic acids can be prepared as described in U.S. Pat. No. 5,476,925, herein incorporated by reference.

Phosphotriester nucleic acids can be prepared as described in U.S. Pat. No. 5,023,243, herein incorporated by reference.

Boranophosphate nucleic acids can be prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone nucleic acids having, for instance, alternating MMI and P═O or P═S linkages can be prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides can be prepared as described in U.S. Pat. Nos. 5,264,562 and 5,264,564, herein incorporated by reference.

Ethylene oxide linked oligonucleosides can be prepared as described in U.S. Pat. No. 5,223,618, herein incorporated by reference.

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers can be used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that can be differentially removed and can be differentially chemically labile, RNA nucleic acids were synthesized.

RNA nucleic acids can be synthesized in a stepwise fashion. In this approach, each nucleotide is added sequentially (3'- to 5'-direction) to a solid support-bound nucleic acid. The first nucleoside at the 3'-end of the chain is covalently attached to a solid support. The nucleotide precursor, a ribonucleoside phosphoramidite, and activator can be added, coupling the second base onto the 5'-end of the first nucleoside. The support is washed and any unreacted 5'-hydroxyl groups can be capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide. Following synthesis, the methyl protecting groups on the phosphates can be cleaved utilizing 1 M disodium-2-carbamoyl-2-cyanoethyl-ene-1,1-dithiolate trihydrate ($S_2Na_2$) in DMF. The deprotection solution is washed from the solid support-bound nucleic acid using water. The support is then treated with 40% methylamine in water. This releases the RNA nucleic acids into solution, deprotects the exocyclic amines, and modifies the 2'-groups. The nucleic acids can be analyzed by anion exchange HPLC at this stage.

The 2'-orthoester groups can be the last protecting groups to be removed. The ethylene glycol monoacetate orthoester protecting group developed by Dharmacon Research, Inc. (Lafayette, Colo.), is one example of a useful orthoester protecting group which, has the following important properties.

It is stable to the conditions of nucleoside phosphoramidite synthesis and nucleic acid synthesis. However, after nucleic acid synthesis the nucleic acid is treated with methylamine which not only cleaves the nucleic acid from the solid support but also removes the acetyl groups from the orthoesters. The resulting 2-ethyl-hydroxyl substituents on the orthoester can be less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with nucleic acid synthesis and yet, when subsequently modified, permits deprotection to be carried out under relatively mild aqueous conditions compatible with the final RNA nucleic acid product.

Additionally, methods of RNA synthesis are well known in the art (Scaringe, S. A. Ph.D. Thesis, University of Colorado, 1996; Scaringe, S. A., et al., J. Am. Chem. Soc., 1998, 120, 11820-11821; Matteucci, M. D. and Caruthers, M. H. J. Am. Chem. Soc., 1981, 103, 3185-3191; Beaucage, S. L. and Caruthers, M. H. Tetrahedron Lett., 1981, 22, 1859-1862; Dahl, B. J., et al., Acta Chem. Scand., 1990, 44, 639-641; Reddy, M. P., et al., Tetrahedron Lett., 1994, 25, 4311-4314; Wincott, F. et al., Nucleic Acids Res., 1995, 23, 2677-2684; Griffin, B. E., et al., Tetrahedron, 1967, 23, 2301-2313; Griffin, B. E., et al., Tetrahedron, 1967, 23, 2315-2331).

Nucleic acids incorporating at least one 2'-O-protected nucleoside may also be prepared. After incorporation and appropriate deprotection the 2'-O-protected nucleoside will be converted to a ribonucleoside at the position of incorporation. The number and position of the 2-ribonucleoside units in the final nucleic acid can vary from one at any site or the strategy can be used to prepare up to a full 2'-OH modified nucleic acid. All 2'-O-protecting groups amenable to the synthesis of nucleic acids are included herein.

In general a protected nucleoside is attached to a solid support by for example a succinate linker. Then the nucleic acid is elongated by repeated cycles of deprotecting the 5'-terminal hydroxyl group, coupling of a further nucleoside unit, capping and oxidation (alternatively sulfurization). In a more frequently used method of synthesis the completed nucleic acid is cleaved from the solid support with the removal of phosphate protecting groups and exocyclic amino protecting groups by treatment with an ammonia solution. Then a further deprotection step is normally required for the more specialized protecting groups used for the protection of 2'-hydroxyl groups which will give the fully deprotected nucleic acid.

An effective 2'-O-protecting group is typically capable of selectively being introduced at the 2'-O-position and can be removed easily after synthesis without the formation of unwanted side products. The protecting group is usually inert to the normal deprotecting, coupling, and capping steps required for oligoribonucleotide synthesis. Examples of protecting groups include tetrahydropyran-1-yl, 4-methoxytetrahydropyran-4-yl, piperidine derivatives (e.g. Fpmp) (Reese et al., Tetrahedron Lett., 1986, (27), 2291), standard 5'-DMT (dimethoxytrityl) group, t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762), fluoride labile and photolabile protecting groups (e.g. the 2-(nitrobenzyl)oxy)methyl (nbm) protecting group (Schwartz et al., Bioorg. Med. Chem. Lett., 1992, (2), 1019)), formaldehyde acetal-derived, 2'-O-protecting groups, 2'-O-alkylated nucleoside phosphoramidites including 2'-O-((triisopropylsilyl)oxy)methyl(2'-O—$CH_2$—O—Si(iPr)$_3$TOM), fluoride labile 5'-O-protecting group (non-acid labile) and an acid labile 2'-O-protecting group (Scaringe, Stephen A., Methods, 2001, (23) 206-217). A particularly useful protection scheme is a 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

RNA synthesis strategies used commercially include 5'-O-DMT-2'-O-t-butyldimethylsilyl (TBDMS), 5'-O-DMT-2'-O-(1(2-fluorophenyl)-4-methoxypiperidin-4-yl) (FPMP), 2'-O-((triisopropylsilyl)oxy)methyl(2'-O—$CH_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc Nucleic acids may also be synthesized via solid phase P(III) phosphoramidite chemistry on an automated synthesizer capable of assembling 96 sequences simultaneously in a 96-well format. Phosphodiester internucleotide linkages can be afforded by oxidation with aqueous iodine. Phosphorothioate internucleotide linkages can be generated by sulfurization utilizing 3,H-1,2 benzodithiole-3-one 1,1 dioxide (Beaucage Reagent) in anhydrous acetonitrile. Standard base-protected beta-cyanoethyldiiso-propyl phosphoramidites can be purchased from commercial vendors (e.g. PE-Applied Biosystems, Foster City, Calif., or Pharmacia, Piscataway, N.J.). Non-standard nucleosides can be synthesized as per standard or patented methods. They can be utilized as base protected beta-cyanoethyldiisopropyl phosphoramidites.

Modified nucleic acid backbones (internucleoside linkages) that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, and each of which is herein incorporated by reference.

Another group of nucleic acids amenable to the methods provided herein include nucleic acid mimetics. The term mimetic as it is applied to nucleic acids is intended to include nucleic acids wherein only the furanose ring or both the furanose ring and the internucleotide linkage can be replaced with novel groups, replacement of only the furanose ring is also referred to in the art as being a sugar surrogate. The heterocyclic base moiety or a modified heterocyclic base moiety is maintained for hybridization with an appropriate target nucleic acid. One such nucleic acid mimetic compound that has been shown to have excellent hybridization properties, is referred to as a peptide nucleic acid (PNA). In PNA nucleic acids, the sugar-backbone of an nucleic acid is replaced with an amide containing backbone, in particular an aminoethylglycine backbone. The nucleobases can be retained and bound directly or indirectly to aza nitrogen atoms of the amide portion of the backbone. Representative U.S. patents that teach the preparation of PNA nucleic acids include, but are not limited to, U.S. Pat. Nos. 5,539,082; 5,714,331; and 5,719,262, each of which is herein incorporated by reference. A discussion of PNA nucleic acids can be found in Nielsen et al., Science, 1991, 254, 1497-1500.

Other nucleic acid mimetics that can be used include nucleosides having sugar moieties that are bicyclic thereby locking the sugar conformational geometry. One example of such a nucleotide is a bicyclic sugar moiety having a 4'-$CH_2$—O-2' bridge. The 2'-O— has been linked via a methylene group to the 4' carbon (see U.S. patent application Publication No. application 2003/0087230). The xylo analog has also been prepared (see U.S. patent application Publication No. 2003/0082807). The bridge for a locked nucleic acid (LNA) may be 4'-(-$CH_2$—$)_2$—O-2' wherein n is 1 or 2 (Kaneko et al., U.S. patent application Publication No. US 2002/0147332, Singh et al., Chem. Commun., 1998, 4, 455-456, also see U.S. Pat. Nos. 6,268,490 and 6,670,461 and U.S. patent application Publication No. US 2003/0207841). However the term locked nucleic acids can also be used in a more general sense to describe any bicyclic sugar moiety that has a locked conformation.

Potent and nontoxic antisense nucleic acids containing LNAs have been described (Wahlestedt et al., Proc. Natl. Acad. Sci. U.S.A., 2000, 97, 5633-5638). The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226. The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity nucleic acid analog with a handle has been described in the art (Singh et al., J. Org. Chem., 1998, 63, 10035-10039). In addition, 2'-Amino- and 2'-methylamino-LNAs have been prepared and the thermal stability of their duplexes with complementary RNA and DNA strands has been previously reported. Also see U.S. Patent Application No. 20050261218.

VI. Assays

The anti-miRNA nucleic acids of SEQ ID NOs: 1-38 may be used in assays to increase a number of genes, such as VEGF and EPO. In turn, these assays may be used to screen for EPO agonists and antagonists.

In another embodiment, anti-miRNA nucleic acids may be easily tested for their ability to hybridize to an RNA molecule and increase expression and/or secretion of various genes, such as EPO, using assays well-known in the art and described herein.

For example, in some assays to test whether expression and/or secretion of EPO increases, a cell expressing a detectable level of EPO is employed. The detectable EPO may be modified to enable detection using an image based instrument platform. For example, a cell may be designed to express a recombinant EPO protein containing a fluorescent protein tag. Alternatively, a detectable anti-EPO antibody may be used to detect EPO levels. The antibody may include a fluorescent or chemiluminescent tag. See Example 3.

A number of fluorescent proteins with various properties are commercially available. An important consideration is that the fluorescent properties of the protein should be compatible with the detection equipment such that it can be efficiently excited by the light source of the platform, and the emission wavelength can be detected. When the fluorescent protein is to be used as a marker of target protein translocation, it is important that the fluorescent protein does not itself direct EPO expression and/or secretion. The fluorescent protein should have strong fluorescence under the conditions tested, to minimize the number of molecules needed. In mammalian cells, Enhanced Green Fluorescent Protein (EGFP) may be desired. Image based instrument platforms appropriate for detection of the recombinant EPO may include GE Healthcare IN Cell 3000, Cellomics ArrayScan, Evotec Opera, CompuCyte ICyte, Molecular Devices Discovery 1, BD Biosciences Atto Pathfinder HT, and others. Manufacturers of the major imaging platforms provide standard algorithms with the instruments. Alternatively, it is possible for users with programming expertise to generate custom algorithms using programs such as MATLAB.

In some embodiments, cells are transiently transfected with nucleic acid. The concentration of nucleic acid used varies from cell line to cell line. To determine the optimal nucleic acid concentration for a particular cell line, the cells are treated with a positive control nucleic acid at a range of concentrations.

Cell-based assays may involve whole cells or cell fractions. Exemplary cell types that can be used according to the methods and assays disclosed herein include, e.g., Kelly cells, HepG2 cells, liver cells, kidney cells, and spleen cells, or any other appropriate cell known in the art.

A variety of useful assays for detecting hybridization of a nucleic acid to an RNA molecule in vitro are known in the art. Hybridization assays include, for example, Northern blots and RNase protection assays, and Southern blots. The nucleic acid or RNA molecule can be labeled with any suitable detectable moiety, such as a radioisotope, fluorochrome, chemiluminescent marker, biotin, or other detectable moiety known in the art that is detectable by analytical methods. High throughput methods employing biochip may be used to screen large populations of nucleic acids. The biochip may include a solid substrate with an attached nucleic acid or RNA molecule. The attached compounds may be at spatially defined addresses on the substrate. More than one nucleic acid or RNA molecule sequence may be used. The nucleic acids or RNA molecules may be attached to the biochip in a wide variety of ways, as will be appreciated by those in the art.

VII. Pharmaceutical Compositions

The nucleic acid can be utilized in pharmaceutical compositions by adding an effective amount to a suitable pharmaceutically acceptable diluent or carrier. The nucleic acids may optionally be useful prophylactically. The resulting pharmaceutical compositions may be used to treat anemia, hemophilia, or sickle cell disease in a subject in need thereof, enhancing erythropoiesis, and increasing EPO levels in a subject. Thus, the nucleic acid may be used for the preparation of a medicament for the treatment of anemia, hemophilia, or sickle cell disease, to enhance erythropoiesis, and to increase EPO levels in a subject.

The nucleic acids, as variously defined herein, and compositions thereof may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative U.S. patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The pharmaceutical compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The subject may be an animal or a human. An animal subject may be a mammal, such as a mouse, a rat, a dog, a guinea pig, a monkey, a non-human primate, a cat or a pig. Non-human primates include monkeys and chimpanzees. A suitable animal subject may be an experimental animal, such as a mouse, rat, mouse, a rat, a dog, a monkey, a non-human primate, a cat or a pig.

In some embodiments, an nucleic acid can be administered to a subject via an oral route of administration. Oral nucleic acid compositions may include one or more "mucosal penetration enhancers," also known as "absorption enhancers" or simply as "penetration enhancers." Accordingly, some embodiments include at least one nucleic acid in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of one or more nucleic acids, without interfering with the activity of the compounds, and in such a manner the compounds can be introduced into the body of an animal without unacceptable side-effects such as toxicity, irritation or allergic response. Certain penetration enhancers have been used to improve the bioavailability of certain drugs. See Muranishi, Crit. Rev. Ther. Drug Carrier Systems, 1990, 7, 1 and Lee et al., Crit. Rev. Ther. Drug Carrier Systems, 1991, 8, 91.

Oral compositions for administration of non-parenteral nucleic acids and compositions may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Other excipients that may be added to oral nucleic acid compositions include surfactants (or "surface-active agents"), which are chemical entities which, when dissolved in an aqueous solution, reduce the surface tension of the solution or the interfacial tension between the aqueous solution and another liquid, with the result that absorption of nucleic acids through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorohemical emulsions, such as FC-43 (Takahashi et al., J. Pharm. Phamacol., 1988, 40, 252).

In some embodiments, nucleic acid compositions for oral delivery comprise at least two discrete phases, which phases may comprise particles, capsules, gel-capsules, microspheres, etc. Each phase may contain one or more nucleic acids, penetration enhancers, surfactants, bioadhesives, effervescent agents, or other adjuvant, excipient or diluent. In some embodiments, one phase comprises at least one nucleic acid and at least one penetration enhancer. In some embodiments, a first phase comprises at least one nucleic acid and at least one penetration enhancer, while a second phase comprises at least one penetration enhancer. In some embodiments, a first phase comprises at least one nucleic acid and at least one penetration enhancer, while a second phase comprises at least one penetration enhancer and substantially no nucleic acid. In some embodiments, at least one phase is compounded with at least one degradation retardant, such as a coating or a matrix, which delays release of the contents of that phase. In some embodiments, a first phase comprises at least one nucleic acid, at least one penetration enhancer, while a second phase comprises at least one penetration enhancer and a release-retardant. In particular embodiments, an oral nucleic acid comprises a first phase comprising particles containing an nucleic acid and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1; Yamamoto et al., J. Pharm. Exp. Ther., 1992, 263, 25; Yamashita et al., J. Pharm. Sci., 1990, 79, 579).

Other excipients include chelating agents, i.e. compounds that remove metallic ions from solution by forming complexes therewith, with the result that absorption of nucleic acids through the alimentary and other mucosa is enhanced. With regard to their use as penetration enhancers, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315). Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1; Buur et al., J. Control Rel., 1990, 14, 43).

Some oral nucleic acid compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of an nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate nucleic acid in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115; Takakura et al., Antisense & Nucl. Acid Drug Dev., 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with an nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

For topical or other administration, nucleic acids and compositions may be encapsulated within liposomes or may form complexes thereto, in particular to cationic liposomes. Alternatively, they may be complexed to lipids, in particular to cationic lipids. Topical formulations are described in detail in U.S. patent application Ser. No. 09/315,298 filed on May 20, 1999, which is incorporated herein by reference in its entirety.

In another embodiment, nucleic acid compositions may contain one or more of the anti-miRNA nucleic acids and compositions targeted to a first miRNA target and one or more additional nucleic acids targeted to a second miRNA target. Alternatively, compositions may contain two or more nucleic acids and compositions targeted to different regions, segments or sites of the same miRNA target. Two or more combined compounds may be used together or sequentially.

A pharmaceutical composition can be micronized or powdered so that it is more easily dispersed and solubilized by the body. Processes for grinding or pulverizing drugs are well known in the art, for example, by using a hammer mill or similar milling device.

Dosage forms (compositions) suitable for internal administration contain from about 1.0 milligram to about 5000 milligrams of active ingredient per unit. In these pharmaceutical compositions, the active ingredient may be present in an amount of about 0.5 to about 95% by weight based on the total weight of the composition. Another convention for denoting the dosage form is in mg per meter squared ($mg/m^2$) of body surface area (BSA). Typically, an adult will have approximately 1.75 $m^2$ of BSA. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one tablet or capsule will provide a dose of 25 mg per kg for that patient. It will provide a dose of only 12.5 mg/kg for a 80 kg patient.

By way of general guidance, for humans a dosage of as little as about 0.25 milligrams (mg) per kilogram (kg) of body weight and up to about 600 mg per kg of body weight is suitable as a therapeutically effective dose. In certain embodiments, from about 1 mg/kg to about 600 mg/kg of body weight is used. Other embodiments include doses range from 50 mg/kg to about 600 mg/kg of body weight, from 100 mg/kg to about 600 mg/kg of body weight, from 200 mg/kg to about 600 mg/kg of body weight, or from 300 mg/kg to about 500 mg/kg of body weight. In some embodiments, a dosage of about 400 mg per kg of body weight is employed.

Intravenously, the certain rates of administration can range from about 1 to about 1000 mg/kg/minute during a constant rate infusion. A pharmaceutical composition can be administered in a single daily dose, or the total daily dosage may be administered in divided doses of two, three, or four times daily. A nucleic acid is generally given in one or more doses on a daily basis or from one to three times a week.

A pharmaceutical composition may be administered by any conventional means available for use in conjunction with pharmaceuticals, either as individual therapeutic agents or in combination with other therapeutic agents.

In another aspect, a pharmaceutical kit is provided. The pharmaceutical kit is useful, for example, for the treatment of anemia, hemophilia, and sickle cell disease, which comprise one or more containers containing a pharmaceutical composition comprising a therapeutically effective amount of a nucleic acid. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit. It should be understood that although the specified materials and conditions are important in practicing the methods described herein, unspecified materials and conditions are not excluded so long as they do not prevent the benefits of the methods from being realized.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention where appropriate, without departing from the scope of the invention.

VIII. Examples

Example 1

In Vitro Screening and Analysis of Anti-miRNAs

The following examples are meant to merely illustrate certain embodiments of the technology disclosed herein, and are not meant to limit the scope of the invention.

A library of 288 sequence-specific anti-miRNA nucleic acids were synthesized using locked nucleic acids (LNA) phosphoramidites. The general procedure employed for the synthesis of LNA oligonucleotides containing phosphodiester internucleotide linkages is set forth below. LNA synthesis was performed on one of the following solid-phase synthesizers using LNA phosphoramidites purchased from Sigma-Proligo®: Applied Biosystems® model ABI 3900 or ABI 394 or MerMase-12. Oligonucleotide chains were built on 3'-dT-column support using iterative cycles of deprotection/activation/coupling and oxidation to form phosphodiester internucleotide linkages. After the final coupling the 5'-dimethoxytrityl protection group was left on to facilitate subsequent purification by solid phase extraction on C-18 column support. The anti-miRNA nucleic acid library was designed to target a collection of 369 human miRNA sequences by perfect complimentary base pairing (see Table 1; http://microrna.sanger.ac.uk/cgi-bin/sequences/mirna_summary.pl?org=hsa). Nucleic acid sequences bearing LNA chemistry provides high-affinity binding to their complimentary miRNA sequences, and provide nuclease stability towards this class of miRNA antagonist. The LNA-based anti-miRNA nucleic acid library was targeted against approximately 80% of the known human miRNAs.

These LNA-based miRNA nucleic acids were arrayed in 96-well plates for cell-based phenotypic screening using Kelly cells, which were obtained from DSMZ (German Collection of Microorganisms and Cell Cultures), Braunschweig, Germany.

TABLE 1

| miRNA | miRNA | miRNA | miRNA |
|---|---|---|---|
| let-7a-1 | miR-125-b-2 | miR-214 | miR-485-3p |
| let-7a-2 | miR-126 | miR-215 | miR-485-5p |

TABLE 1-continued

| miRNA | miRNA | miRNA | miRNA |
|---|---|---|---|
| let-7a-3 | miR-126* | miR-216 | miR-488 |
| let-7b | miR-127 | miR-217 | miR-489 |
| let-7c | miR-128a | miR-218-1 | miR-490 |
| let-7d | miR-128b | miR-218-2 | miR-491 |
| let-7e | miR-129-1 | miR-219-1 | miR-492 |
| let-7f-1 | miR-129-2 | miR-219-2 | miR-493 |
| let-7f-2 | miR-130a | miR-220 | miR-494 |
| let-7g | miR-130b | miR-221 | miR-495 |
| let-7i | miR-132 | miR-222 | miR-496 |
| miR-1-1 | miR-133a-1 | miR-223 | miR-497 |
| miR-1-2 | miR-133a-2 | miR-224 | miR-498 |
| miR-7-1 | miR-133b | miR-296 | miR-499 |
| miR-7-2 | miR-134 | miR-299-3p | miR-500 |
| miR-7-3 | miR-135a-1 | miR-299-5p | miR-501 |
| miR-9-1 | miR-135a-2 | miR-301 | miR-502 |
| miR-9-2 | miR-135b | miR-302a | miR-503 |
| miR-9-3 | miR-136 | miR-302b | miR-504 |
| miR-9*-1 | miR-137 | miR-302c | miR-505 |
| miR-9*-2 | miR-138-1 | miR-302d | miR-506 |
| miR-9*-3 | miR-138-2 | miR-302a* | miR-507 |
| miR-10a | miR-139 | miR-302b* | miR-508 |
| miR-10b | miR-140 | miR-302c* | miR-509 |
| miR-15a | miR-141 | miR-320 | miR-510 |
| miR-15b | miR-142-3p | miR-323 | miR-511-1 |
| miR-16-1 | miR-142-5p | miR-324-3p | miR-511-2 |
| miR-16-2 | miR-143 | miR-324-5p | miR-512-1-3p |
| miR-17-3p | miR-144 | miR-325 | miR-512-2-3p |
| miR-17-5p | miR-145 | miR-326 | miR-512-1-5p |
| miR-18a | miR-146a | miR-328 | miR-512-2-5p |
| miR-18b | miR-146b | miR-329-1 | miR-513-1 |
| miR-19a | miR-147 | miR-329-2 | miR-513-2 |
| miR-19b-1 | miR-148a | miR-330 | miR-514-1 |
| miR-19b-2 | miR-148b | miR-331 | miR-514-2 |
| miR-20a | miR-149 | miR-335 | miR-514-3 |
| miR-20b | miR-150 | miR-337 | miR-515-1-3p |
| miR-21 | miR-151 | miR-338 | miR-515-2-3p |
| miR-22 | miR-152 | miR-339 | miR-515-1-5p |
| miR-23a | miR-153-1 | miR-340 | miR-515-2-5p |
| miR-23b | miR-153-2 | miR-342 | miR-516-1-3p |
| miR-24-1 | miR-154 | miR-345 | miR-516-2-3p |
| miR-24-2 | miR-154* | miR-346 | miR-516-3-3p |
| miR-25 | miR-155 | miR-361 | miR-516-4-3p |
| miR-26a-1 | miR-181a | miR-362 | miR-516-1-5p |
| miR-26a-2 | miR-181b-1 | miR-363 | miR-516-2-5p |
| miR-26b | miR-181b-2 | miR-365-1 | miR-517-a* |
| miR-27a | miR-181c | miR-365-2 | miR-517-b* |
| miR-27b | miR-181d | miR-367 | miR-517-c* |
| miR-28 | miR-182 | miR-368 | miR-517a |
| miR-29a | miR-182* | miR-369-3p | miR-517b |
| miR-29b-1 | miR-183 | miR-369-5p | miR-517c |
| miR-29b-2 | miR-184 | miR-370 | miR-518a-1 |
| miR-29c | miR-185 | miR-371 | miR-518a-2 |
| miR-30a-3p | miR-186 | miR-372 | miR-518b |
| miR-30a-5p | miR-187 | miR-373 | miR-518c |
| miR-30b | miR-188 | miR-373* | miR-518d |
| miR-30c-1 | miR-189 | miR-374 | miR-518e |
| miR-30c-2 | miR-190 | miR-375 | miR-518f |
| miR-30d | miR-191 | miR-376a | miR-518a-2* |
| miR-30e-3p | miR-191* | miR-376b | miR-518c* |
| miR-30e-5p | miR-192 | miR-377 | miR-518f* |
| miR-31 | miR-193a | miR-378 | miR-519a-1 |
| miR-32 | miR-193b | miR-379 | miR-519a-2 |
| miR-33 | miR-194-1 | miR-380-3p | miR-519b |
| miR-34a | miR-194-2 | miR-380-5p | miR-519c |
| miR-34b | miR-195 | miR-381 | miR-519d |
| miR-34c | miR-196a-1 | miR-382 | miR-519e |
| miR-92-1 | miR-196a-2 | miR-383 | miR-519e* |
| miR-92-2 | miR-196b | miR-384 | miR-520a |
| miR-93 | miR-197 | miR-409-3p | miR-520b |
| miR-95 | miR-198 | miR-409-5p | miR-520c |
| miR-96 | miR-199a-1 | miR-410 | miR-520d |
| miR-98 | miR-199a*-1 | miR-412 | miR-520e |
| miR-99a | miR-199a-2 | miR-422a | miR-520f |
| miR-99b | miR-199a*-2 | miR-422b | miR-520g |
| miR-100 | miR-199b | miR-423 | miR-520h |
| miR-101-1 | miR-200a | miR-424 | miR-520a* |
| miR-101-2 | miR-200b | miR-425 | miR-520d* |
| miR-103-1 | miR-200c | miR-429 | miR-521-1 |

TABLE 1-continued

| miRNA | miRNA | miRNA | miRNA |
|---|---|---|---|
| miR-103-2 | miR-200a* | miR-431 | miR-521-2 |
| miR-105-1 | miR-202 | miR-432 | miR-522 |
| miR-105-2 | miR-202* | miR-432* | miR-523 |
| miR-106a | miR-203 | miR-433 | miR-524 |
| miR-106b | miR-204 | miR-448 | miR-524* |
| miR-107 | miR-205 | miR-449 | miR-525 |
| miR-122a | miR-206 | miR-450-1 | miR-525* |
| miR-124a-1 | miR-208 | miR-450-2 | miR-526c |
| miR-124a-2 | miR-210 | miR-451 | miR-526a |
| miR-124a-3 | miR-211 | miR-452 | miR-526b |
| miR-125a | miR-212 | miR-452* | miR-526b* |
| miR-125-b-1 | miR-213 | miR-453 | miR-527 |

The neuroblastoma cell line, Kelly, can be stimulated to secrete EPO under hypoxic conditions. The involvement of the transcription factor, HIF, in the secretion of EPO in this cell line is supported by its ability to produce EPO under normoxic conditions upon down regulation of HIF-Prolyl Hydroxylase, the enzyme that oxidizes through hydroxylation specific Proline residues in HIF, preventing eventual proteasomal degradation. The stabilization of HIF leads to the up-regulation of a large number of genes that contain HIF binding sites in the upstream promoter elements. Among others, HIF-regulated genes include Erythropoietin (EPO) and Vascular Endothelial Growth Factor (VEGF).

An siRNA against HIF-Prolyl Hydroxylase 2 (siPHD2) that stimulates EPO production in Kelly cells was used to optimize the assay conditions for the microRNA interference screen. This led to identification of a ~1500-fold window above the background with ~60,000 Kelly cells transfected with 20 nM siPHD2 siRNA after 72 hrs. These conditions were used for the screen in which siPHD2 served as the positive control.

Kelly cells grown in DMEM supplemented with 10% Fetal Bovine Serum and non essential amino acids at 37° C. and 5% $CO_2$ were seeded at a density of ~60,000 cells/well in 96-well culture plates the day before transfection. Each plate of LNA-based miRNA interference library was transfected on duplicate Kelly cell plates using 0.24% Lipofectamine2000 according to Manufacturer's instructions. EPO and VEGF levels were measured by using MSD ELISA assay. Briefly; cell culture supernatants collected 72 hours after transfection were used to measure the production of EPO and VEGF. The cytokines were quantified by the electro-chemiluminescence multiplex system Sector 2400 imager from Meso Scale Discovery (MSD; Gaithersburg, Md.). Supernatants were incubated in 96 well plates pre-coated with antibodies to EPO and VEGF. The bound cytokines were detected with a second capture antibody conjugated with a sulfo-tag (MSD proprietary) using electroluminescence signal. A dilution series of EPO and VEGF standard were included on each screen plate.

This initial screen identified primary LNA sequences that increase expression and/or secretion of EPO at a concentration of 400 nM. See FIGS. 2-6. In the primary 400 nM screen, LNAs that gave the signal above one standard deviation (STDV) of the mean of each plate average were designated as positive hits. The anti-miRNA portion of the nucleic acids identified as positive hits are set forth in Table 2. Due to the use of a deoxythymidine (dT) column during synthesis, the nucleic acids identified in this Example 1 consist of the stated sequences in Table 2 and a deoxy-T at the 3' end of the sequences. One of skill in the art will immediately recognize that SEQ ID Nos: 1 to 38 per se do not include the 3' dT, and where one of SEQ ID Nos: 1 to 38 are claimed or referred to within Sections Ito VII above, the 3' dT is not intended to be included in the nucleic acid sequence. The sequences of the target miRNAs are provided in Table 3.

TABLE 2

| Anti-miRNA nucleic acid | Anti-miRNA Nucleic Acid Sequence (3' to 5') | miRNA Target |
|---|---|---|
| SEQ ID NO: 1 | TTGGGCATCTAGGCTTGAACA | miR-100 |
| SEQ ID NO: 2 | TCGTCGTAACATGTCCCGATA | miR-103-1, 2, miR-107 |
| SEQ ID NO: 3 | GTTGCCTTAGGGTTTTCGTCG | miR-191 |
| SEQ ID NO: 4 | AGGTCGAGGATATACTACGGA | miR-337 |
| SEQ ID NO: 5 | TTCACGAAGGAAAATCTCCCA | miR-520-f |
| SEQ ID NO: 6 | TGTTTCACGAAGGGAAATCTC | miR-520-g, h |
| SEQ ID NO: 7 | GATGTTTCCCTTCGTGAAAGA | miR-524* |
| SEQ ID NO: 8 | CCAGGTCTCCCCTCTATCC | miR-198 |
| SEQ ID NO: 9 | ATACACCCTACCATTTAACGA | miR-299-3p |
| SEQ ID NO: 10 | ACCAAATGGCAGGGTGTATGT | miR-299-5p |
| SEQ ID NO: 11 | AAAGTTCGGTCCCCCGCAAAA | miR-498 |
| SEQ ID NO: 12 | GAGATCTCCCTTCGTGAAAGA | miR-518-f* |
| SEQ ID NO: 13 | ACTCCATCATCCAACATATCA | let-7-a-1, 2, 3 |
| SEQ ID NO: 14 | ACTCCATCATCCAACA | let-7-b, c |
| SEQ ID NO: 15 | ACTCCATCATCAAACA | let-7-g-I |
| SEQ ID NO: 16 | ACCTTCTGATCACTAAAACAA | miR-7-1, 2, 3 |
| SEQ ID NO: 17 | ATTTCGATCTATTGGCTTTCA | miR-9*-1, 2, 3 |
| SEQ ID NO: 18 | ACATTTGTAGGGGCTGACCTT | miR-30-d |
| SEQ ID NO: 19 | ATCCGTCACAGTAATCGACTA | miR-34-b |
| SEQ ID NO: 20 | ACTCCATCATTCAACATAACA | miR-98 |
| SEQ ID NO: 21 | AGTGTCACTTGGCCAGAGAAA | miR-128-a, b |
| SEQ ID NO: 22 | ATTGTCAGATGTCGGTACCAG | miR-132 |
| SEQ ID NO: 23 | ATACCGAAAAGTAAGGATACA | miR-133-a, b, 1, 2 |
| SEQ ID NO: 24 | ATTAGAGTCGACCGTTGACAC | miR-216 |
| SEQ ID NO: 25 | AACGTATACATCCTACAGGGT | miR-448 |
| SEQ ID NO: 26 | ACAAACGTCTCCTTTGACTCT | miR-452 |
| SEQ ID NO: 27 | TCACCCCTTGGGAAGGTACTC | miR-491 |
| SEQ ID NO: 28 | GTCGTCGTGTGACACCAAACA | miR-497 |
| SEQ ID NO: 29 | TTTCACGAAGGAAAATCTCCC | miR-520-b, c |
| SEQ ID NO: 30 | GCCCTTTCATCATTGCACTG | miR-130-a, b |
| SEQ ID NO: 31 | GTAGTGCTTTCTACTTTATG | miR-142-5p |
| SEQ ID NO: 32 | CGGGACTTTGAGGGCCAGTT | miR-193-b |
| SEQ ID NO: 33 | ACCCACAGACGTACCAATCA | miR-509 |
| SEQ ID NO: 34 | CCTCTATAGGGAAGCGCGTT | miR-523 |

TABLE 2-continued

| Anti-miRNA nucleic acid | Anti-miRNA Nucleic Acid Sequence (3' to 5') | miRNA Target |
|---|---|---|
| SEQ ID NO: 35 | GAAAGTGCATCCCTCTGGAG | miR-525 |
| SEQ ID NO: 36 | GAAAGTGCTTCCCTCTAGAG | miR-526-a |
| SEQ ID NO: 37 | GAAAGCGCTTCCCTCTAGAG | miR-526-c |
| SEQ ID NO: 38 | CTCTAAAGGGGAGCGCTTTG | miR-518-b |

TABLE 3

| anti-miRNA | Target miRNA | Target miRNA Sequence (5'to 3') | Target miRNA |
|---|---|---|---|
| SEQ ID NO: 1 | miR-100 | AACCCGUAGAUCCGAACUUGU | SEQ ID NO: 39 |
| SEQ ID NO: 2 | miR-103-1, 2 | AGCAGCAUUGUACAGGGCUAU | SEQ ID NO: 40 |
| SEQ ID NO: 2 | miR-107 | AGCAGCAUUGUACAGGGCUAU | SEQ ID NO: 41 |
| SEQ ID NO: 3 | miR-191 | CAACGGAAUCCCAAAAGCAGC | SEQ ID NO: 42 |
| SEQ ID NO: 4 | miR-337 | UCCAGCUCCUAUAUGAUGCCU | SEQ ID NO: 43 |
| SEQ ID NO: 5 | miR-520-f | AAGUGCUUCCUUUUAGAGGGU | SEQ ID NO: 44 |
| SEQ ID NO: 6 | miR-520-g, h | ACAAAGUGCUUCCCUUUAGAG | SEQ ID NO: 45 |
| SEQ ID NO: 7 | miR-524* | CUACAAAGGGAAGCACUUUCU | SEQ ID NO: 46 |
| SEQ ID NO: 8 | miR-198 | GGUCCAGAGGGGAGAUAGG | SEQ ID NO: 47 |
| SEQ ID NO: 9 | miR-299-3p | UAUGUGGGAUGGUAAACCGCU | SEQ ID NO: 48 |
| SEQ ID NO: 10 | miR-299-5p | UGGUUUACCGUCCCACAUACA | SEQ ID NO: 49 |
| SEQ ID NO: 11 | miR-498 | UUUCAAGCCAGGGGGCGUUUU | SEQ ID NO: 50 |
| SEQ ID NO: 12 | miR-518*-f | CUCUAGAGGGAAGCACUUUCU | SEQ ID NO: 51 |
| SEQ ID NO: 13 | let-7-a-1, 2, 3 | UGAGGUAGUAGGUUGUAUAGU | SEQ ID NO: 52 |
| SEQ ID NO: 14 | let-7-b, c | UGAGGUAGUAGGUUGU | SEQ ID NO: 53 |
| SEQ ID NO: 15 | let-7-g-I | UGAGGUAGUAGUUUGU | SEQ ID NO: 54 |
| SEQ ID NO: 16 | miR-7-1, 2, 3 | UGGAAGACUAGUGAUUUUGUU | SEQ ID NO: 55 |
| SEQ ID NO: 17 | miR-9*-1, 2, 3 | UAAAGCUAGAUAACCGAAAGU | SEQ ID NO: 56 |
| SEQ ID NO: 18 | miR-30-d | UGUAAACAUCCCCGACUGGAA | SEQ ID NO: 57 |
| SEQ ID NO: 19 | miR-34-b | UAGGCAGUGUCAUUAGCUGAU | SEQ ID NO: 58 |
| SEQ ID NO: 20 | miR-98 | UGAGGUAGUAAGUUGUAUUGU | SEQ ID NO: 59 |
| SEQ ID NO: 21 | miR-128-a, b | UCACAGUGAACCGGUCUCUUU | SEQ ID NO: 60 |
| SEQ ID NO: 22 | miR-132 | UAACAGUCUACAGCCAUGGUC | SEQ ID NO: 61 |
| SEQ ID NO: 23 | miR-133-a, b, 1, 2 | UAUGGCUUUUCAUUCCUAUGU | SEQ ID NO: 62 |
| SEQ ID NO: 24 | miR-216 | UAAUCUCAGCUGGCAACUGUG | SEQ ID NO: 63 |
| SEQ ID NO: 25 | miR-448 | UUGCAUAUGUAGGAUGUCCCA | SEQ ID NO: 64 |
| SEQ ID NO: 26 | miR-452 | UGUUUGCAGAGGAAACUGAGA | SEQ ID NO: 65 |
| SEQ ID NO: 27 | miR-491 | AGUGGGGAACCCUUCCAUGAG | SEQ ID NO: 66 |
| SEQ ID NO: 28 | miR-497 | CAGCAGCACACUGUGGUUUGU | SEQ ID NO: 67 |
| SEQ ID NO: 29 | miR-520-b,c | AAAGUGCUUCCUUUUAGAGGG | SEQ ID NO: 68 |
| SEQ ID NO: 30 | miR-130-a,b | CAGUGCAAUGAUGAAAGGGCA | SEQ ID NO: 69 |
| SEQ ID NO: 31 | miR-142-5p | CAUAAAGUAGAAAGCACUAC | SEQ ID NO: 70 |

TABLE 3-continued

| anti-miRNA | Target miRNA | Target miRNA Sequence (5'to 3') | Target miRNA |
|---|---|---|---|
| SEQ ID NO: 32 | miR-193-b | AACUGGCCCUCAAAGUCCCGC | SEQ ID NO: 71 |
| SEQ ID NO: 33 | miR-509 | UGAUUGGUACGUCUGUGGGUA | SEQ ID NO: 72 |
| SEQ ID NO: 34 | miR-523 | AACGCGCUUCCCUAUAGAGGG | SEQ ID NO: 73 |
| SEQ ID NO: 35 | miR-525 | CUCCAGAGGGAUGCACUUUCU | SEQ ID NO: 74 |
| SEQ ID NO: 36 | miR-526-a | CUCUAGAGGGAAGCACUUUCU | SEQ ID NO: 75 |
| SEQ ID NO: 37 | miR-526-c | CUCUAGAGGGAAGCGCUUUCU | SEQ ID NO: 76 |
| SEQ ID NO: 38 | miR-518-b | CAAAGCGCUCCCCUUUAGAGG | SEQ ID NO: 77 |

Figure 7:
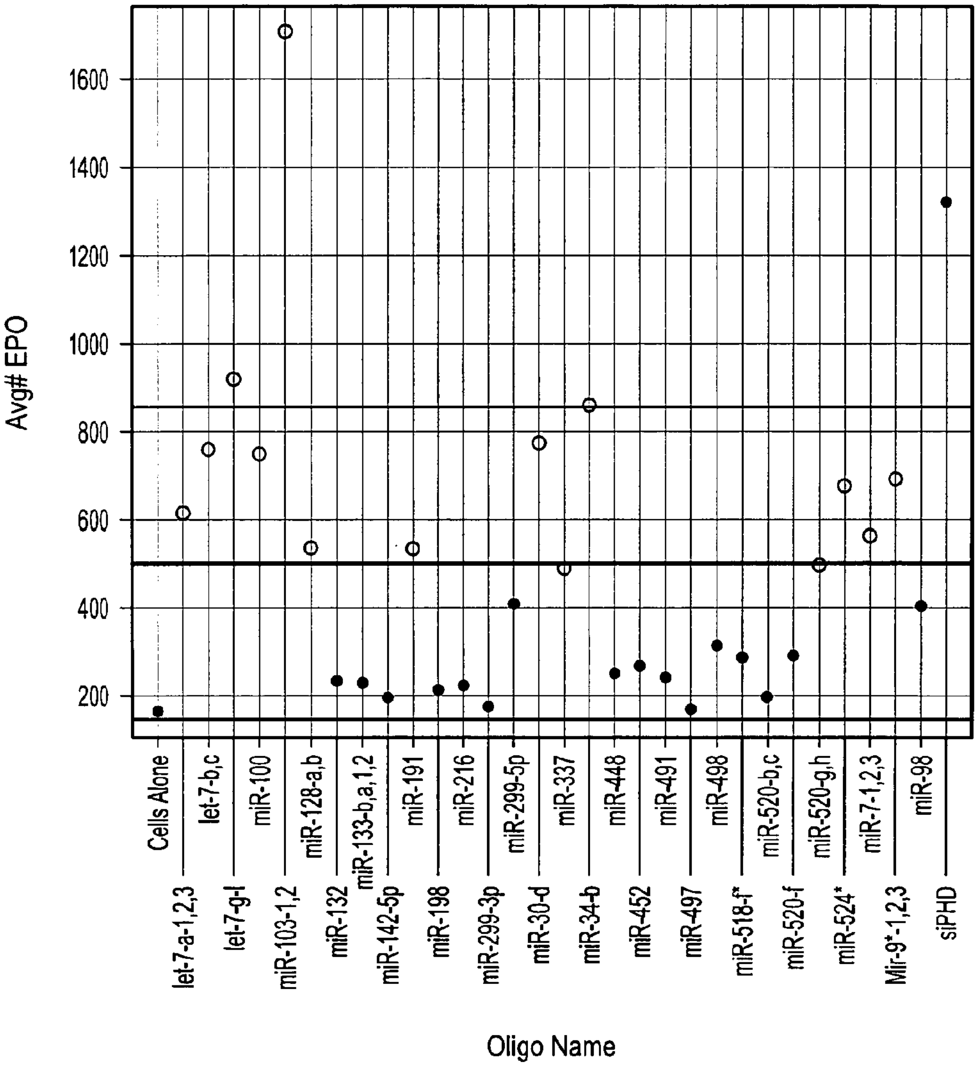
FIG. 7 illustrates data collected in a screen of nucleic acids at a concentration of 40 nM in Kelly cells targeting the noted microRNAs.
Figure 8:
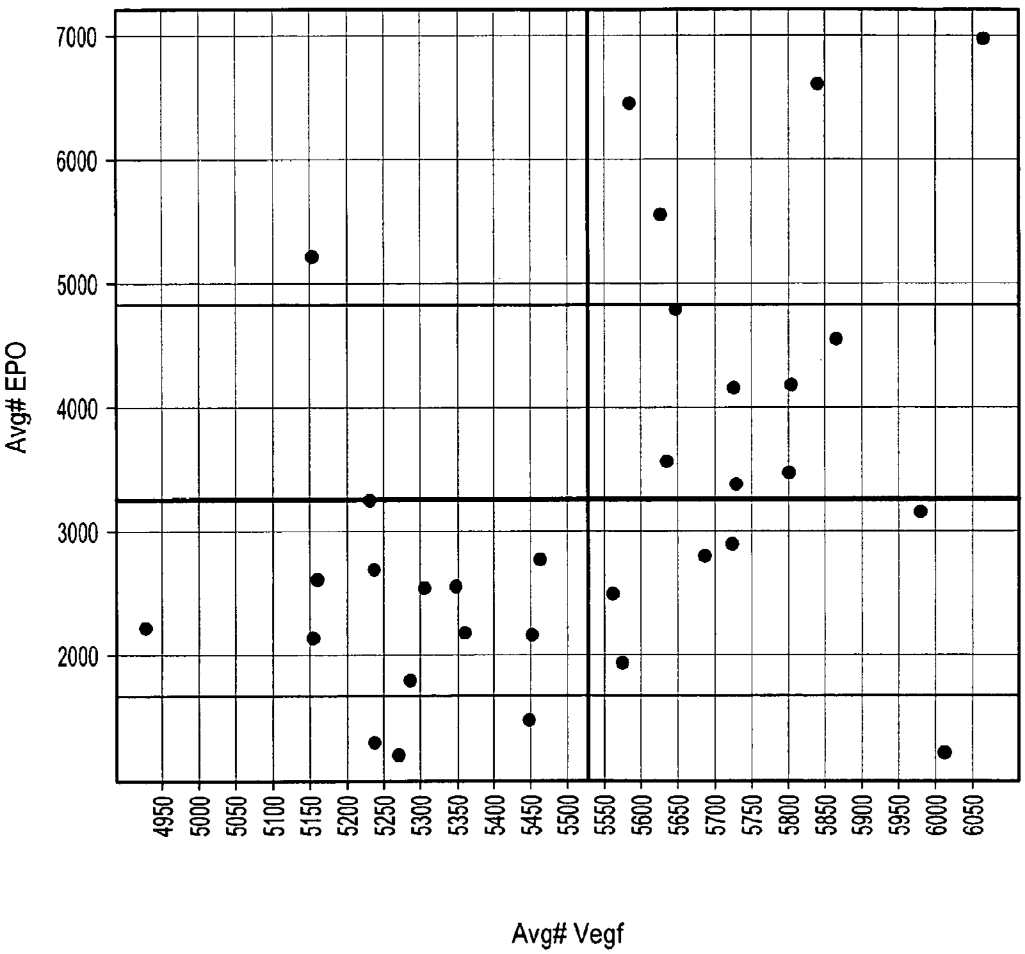
FIGS. 8 and 9 illustrate data collected in a screen of nucleic acids at a concentration of 20 nM in Kelly cells targeting the noted microRNAs.
Figure 9:
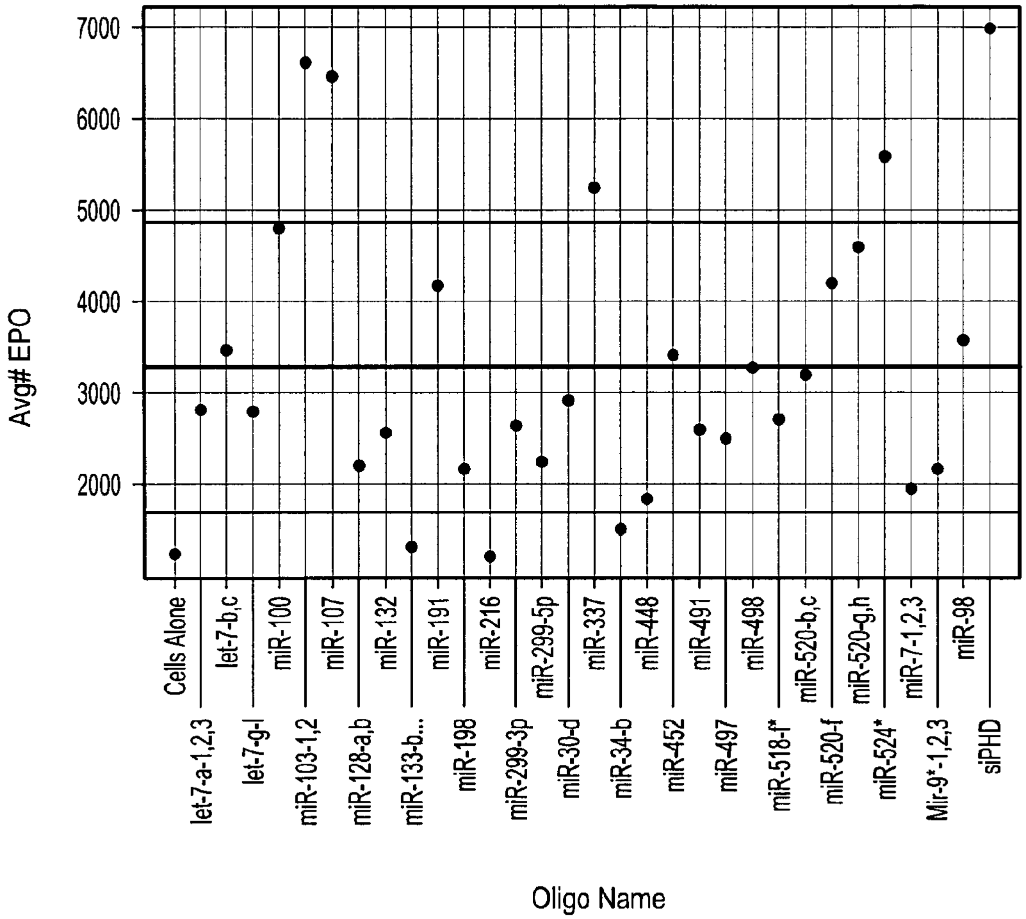
Figure 10:
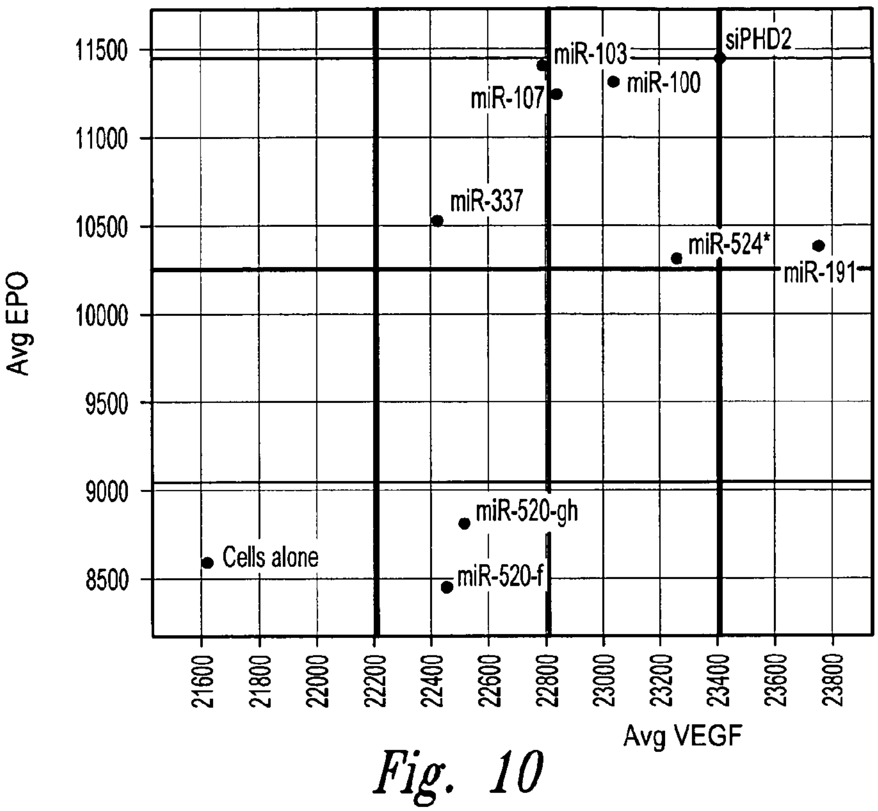
FIG. 10 illustrates data collected in a screen of nucleic acids at a concentration of 20 nM in HEPG2 cells targeting the noted microRNAs.

In subsequent screens, the LNA sequences designated as primary hits in the 400 nM screen were transfected at 100 nM, 40 nM, and 20 nM. See FIGS. 7, 8, and 9. In FIG. 8, results are provided for selected microRNAs that increase EPO preferentially over VEGF in Table 4 below. Certain LNA sequences in the 20 nM screen for Kelly cells were then tested in HEPG2 cells. The results are provided in FIG. 10.

TABLE 4

| Anti-miRNA Nucleic acid | Avg#EPO | Avg#Vegf |
|---|---|---|
| SEQ ID NO: 10 | 2231 | 4930 |
| SEQ ID NO: 8 | 2148 | 5158 |
| SEQ ID NO: 4 | 5231 | 5159 |
| SEQ ID NO: 9 | 2619 | 5165 |
| SEQ ID NO: 11 | 3253 | 5234 |
| SEQ ID NO: 12 | 2690 | 5240 |

Example 2

In Vivo Testing of Anti-miRNAs

In vivo testing of anti-miRNA nucleic acid sequences was performed to establish proof of concept of gene regulation by inhibiting miRNAs that down-regulate genes such as EPO and VEGF. In this study two miRNA sequences, miR-103-1,2 (SEQ ID NO:40) and miR-524* (SEQ ID NO:46) were targeted in vivo by their complimentary anti-miRNA sequences shown below.

Target miR-103-1, 2:
(SEQ ID NO: 40)
5'-AGCAGCAUUGUACAGGGCUAU-3'
Anti-miR-103-1, 2:
(SEQ ID NO: 78)
5'-C*C*T*G*U*A*C*A*A*U*G*C*U*G*C*T*t-3'
Target miR-524*:
(SEQ ID NO: 46)
5'-CUACAAAGGGAAGCACUUUCU-3'
Anti-miR-524*:
(SEQ ID NO: 79)
5'-C*T*G*C*U*T*C*C*C*U*U*T*G*T*A*G*t-3'

The miRNAs were targeted at their 5' seed region by 17-nt anti-miRNA sequences. The anti-miRNA sequences shown above were completely phosphorothioated (indicated by *) and chemically modified as follows: nucleotides in bold carry LNA modification and those in italics have a 2'-OMe modification. An inverted deoxy thymidine residue was incorporated at the 3' end to prevent nucleotide cleavage by exonucleases and is indicated by a lower case t.

LNA-modified anti-miRNA sequences were formulated in phosphate-buffered saline (PBS) and were administered by intravenous injection (tail vein) into female Sprague-Dawley rats weighing approximately 200-225 g. The experimental design consisted of 4 groups with 3 animals per group:

Group A: PBS vehicle control
Group B: anti-miR-524* at 20 mg/kg
Group C: anti-miR-103-1,2 at 10 mg/kg
Group D: anti-miR-103-1,2 at 20 mg/kg Blood samples were taken (150-200 uL/time point) three days prior to administration of the anti-miRNA sequences to establish baseline levels of EPO and VEGF. The anti-miRNA sequences were administered once. Blood samples were collected into EDTA microtainers at 4, 6, 8, 24, 48, 72, 96 and 168 hours post-administration. Plasma VEGF levels (ng/ml) were measured using established protocols, assay kits, and instrumentation from Meso Scale Discovery™ (Gaithersburg, Md.). Plasma samples from rats dosed with miRNA or controls were subjected to the Meso Scale Discovery mouse/rat serum/plasma hypoxia panel assay (Meso Scale Discovery, Gaithersburg Md., catalog number K11123C-3). This assay shows a linear dynamic range for rat EPO in plasma from 16 pg/ml to 10,000 pg/ml with a typical lower limit of quantitation of ~10 pg/ml. The linear dynamic range for rat VEGF in plasma is 60 pg/ml to 10,000 pg/ml with a typical lower limit of quantitation of ~40 pg/ml. The assay was performed according to the manufacturer's instructions. In brief, samples or calibrators (25 uL) were first diluted 2-fold in diluent H assay buffer then 25 uL was added to each well. Plates were incubated for two hours at room temperature with agitation then washed three times with 300 μL PBS using a Biotek ELx405 micorplate washer (BioTek Instruments, Winooski, Vt.). Next, 25 μl SULFO-TAG anti-mouse/rat EPO antibody plus SULFO-TAG anti mouse/rat VEGF antibody, diluted in antibody diluent GF1, was added and plates were incubated for two hours at room temperature with agitation. The plates were washed again three times with 300 μL PBS before 150 μL Read Buffer T was added. Plates were read immediately with the MSD SECTOR Imager 6000 (Meso Scale Discovery, Gaithersburg Md.). Background signal was subtracted and the concentration of circulating EPO and VEGF was derived from interpolation of the rat EPO and rat VEGF standard curves. Analysis was performed with Graphpad Prism 5.01.

Figure 11:
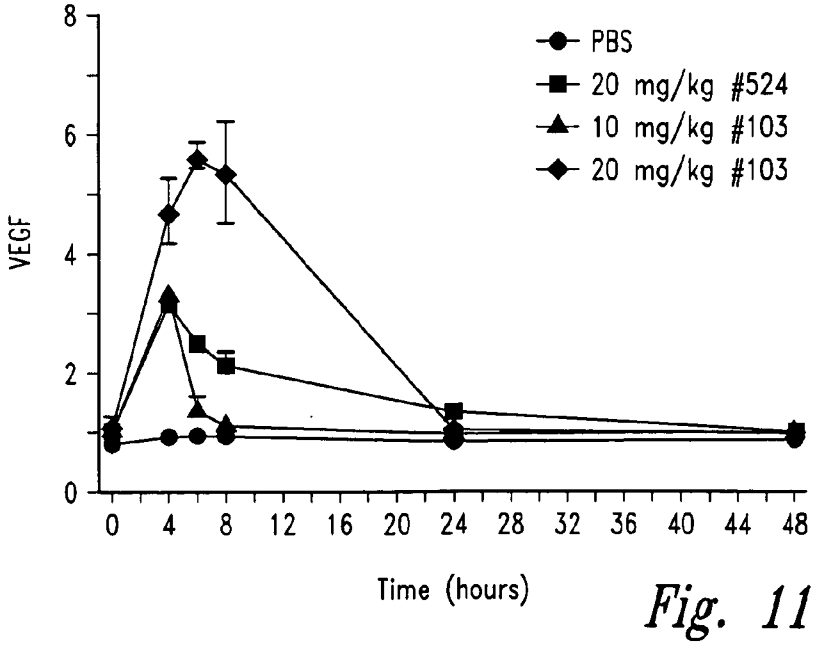
FIG. 11 shows an increase in the amount of VEGF in rat plasma (ng/ml) post administration of a single intravenous dose of anti-miR-103-1,2 (SEQ ID NO: 78) or anti-miR-524* (SEQ ID NO: 79).
Figure 12:
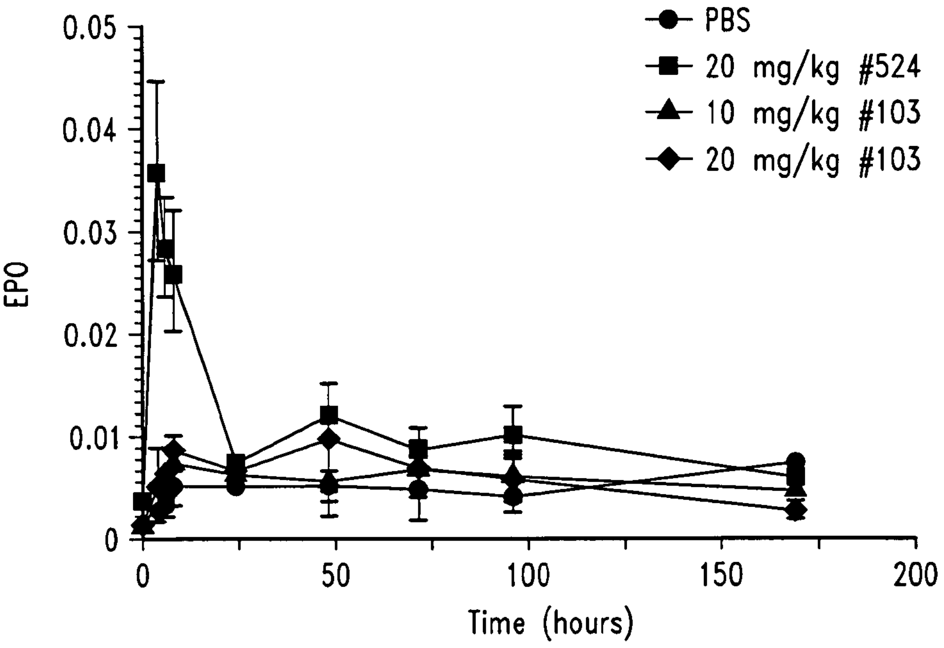
FIG. 12 shows an increase in the amount of VEGF in rat plasma (ng/ml) post administration of a single intravenous dose of anti-miR-103-1,2 (SEQ ID NO: 78) or anti-miR-524* (SEQ ID NO: 79).

Notably, a single dose intravenous administration generated an increase in VEGF in rat plasma within 2 hours for both the anti-miR-103-1,2 (SEQ ID NO: 78) and anti-miR-524* (SEQ ID NO: 79) sequences. FIG. 11 shows the ng/ml of VEGF in relation to hours post administration. There is a clear dose response to anti-miR-103-1,2 (SEQ ID NO: 78) as measured by increasing VEGF stimulation/stabilization. The VEGF levels decayed over time and reached background level within 24 hours. FIG. 12 shows the change in EPO levels (ng/ml) over time.

Figure 13A:
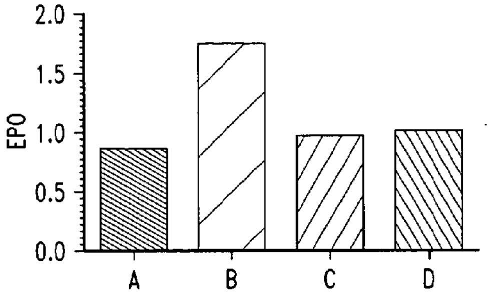
FIG. 13A shows the average of 3 test animals and 13B shows data for the individual test animals for the amount of EPO induced by the test compounds.
Figure 13B:
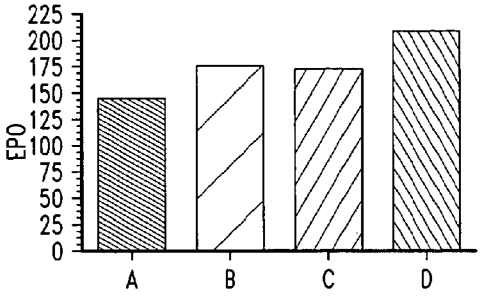
FIG. 13C shows the average of 3 test animals and 13D shows data for the individual test animals for the amount of VEGF induced by the test compounds. The data is presented as the area under the curve (AUC) for the ng VEGF or EPO multiplied by time (168 hours) on a per/ml basis. "A" is the phosphate buffered saline control; "B" is 20 mg/kg of anti-miR-524* (SEQ ID NO: 79); "C" is 10 mg/kg of anti-miR-103-1,2 (SEQ ID NO: 78); and "D" is 20 mg/kg of anti-miR-103-1,2 (SEQ ID NO: 78).
Figure 13C:
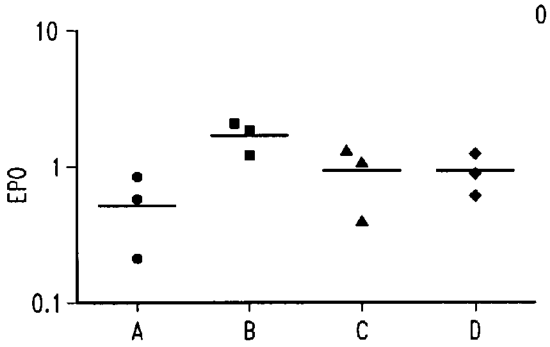
Figure 13D:
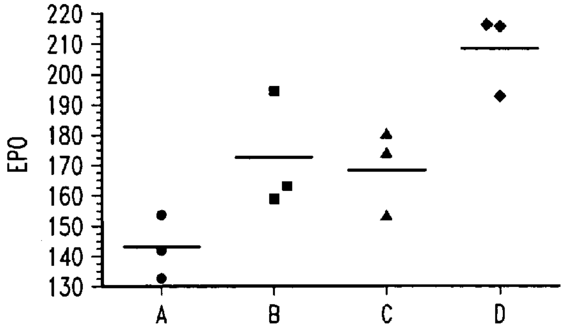

FIG. 13A shows the amount of EPO induced (the average of 3 test animals) and 13B shows the amount of EPO induced for individual test animals. FIG. 13C shows the amount of VEGF induced (the average of 3 test animals) and 13D shows the amount of VEGF induced for individual test animals. The data is presented as the area under the curve (AUC) for the ng VEGF or EPO multiplied by time (168 hours) on a per/ml basis. "A" is the phosphate buffered saline control; "B" is 20 mg/kg of anti-miR-524* (SEQ ID NO: 79); "C" is 10 mg/kg of anti-miR-103-1,2 (SEQ ID NO: 78); and "D" is 20 mg/kg of anti-miR-103-1,2 (SEQ ID NO: 78). While the in vivo data for EPO was determined to not be statistically significant over the noise of the assay, the in vivo data for VEGF induction was statistically significant and is consistent with that results observed in vitro (above). These experiments provide proof of principle that the anti-miRNA nucleic acids can cause an increase in and/or stabilize select genes, such as VEGF and EPO under the right conditions (as shown by in vitro analysis).

Pharmacokinetic studies on plasma drug levels were measured at each time point. In addition, tissue samples were harvested at 168 hour post-administration and snap-frozen in liquid nitrogen for later analysis. Tissue samples included liver, kidney, spleen, heart, and bone marrow.

MiRna levels in plasma and tissue samples was analyzed using standard ELISA techniques. In brief, standard 96-well ELISA plates were coated with streptavidin solution, (such as 2.5 μg/ml of commercially available streptavidin diluted in 50 mM Tris Buffer, pH 8.0 or any other suitable buffer. Plates were sealed and incubated overnight at 2-8° C. The plates were washed using standard methods. Approximately 150 μl of I-Block™ (Applied Biosystems, Foster City, Calif.) was added to each well. Plates were sealed and incubated for 1-2 hours at room temperature and then washed. Serially diluted tissue lysates and plasma samples were added to the plates and incubated for one hour at room temperature. The plates were washed and biotinylated capture oligo (an oligo that is complementary to part of the anti-miRNA sequence being analyzed) and digoxin-labeled detection oligo (an oligo that is complementary to part of the anti-miRNA sequence being analyzed but is not overlapping with the capture oligo) were diluted in a suitable buffer, added to appropriate wells, and incubated at room temperature for approximately one hour. The plates were washed and standards and samples (i.e., containing the anti-miRNA to be measured) were added and incubated at room temperature for approximately 1 hour. The plates were washed and anti-digoxin polyclonal antibody was diluted in a suitable buffer such as 1×PBS (Phosphate Buffered Saline), added to the plates, and incubated at room temperature for approximately one hour. The plates were washed and using standard reagents and protocols from Pierce Protein Research Product's Femto SuperSignal® ELISA (Thermo Fisher Scientific, Rockford, Ill.), the substrate was prepared, added to the plates, and the resultant signal analyzed.

Figure 14A:
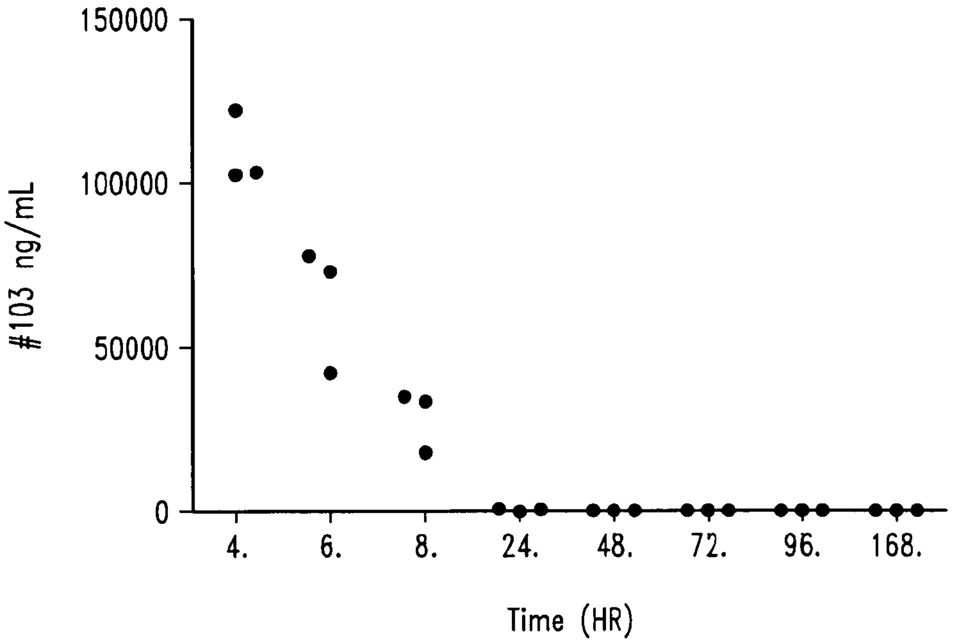
FIG. 14A shows the plasma clearance for the 20 mg/kg dose in individual animals of anti-miR-103-1,2 (SEQ ID NO: 78) over time.
Figure 14B:
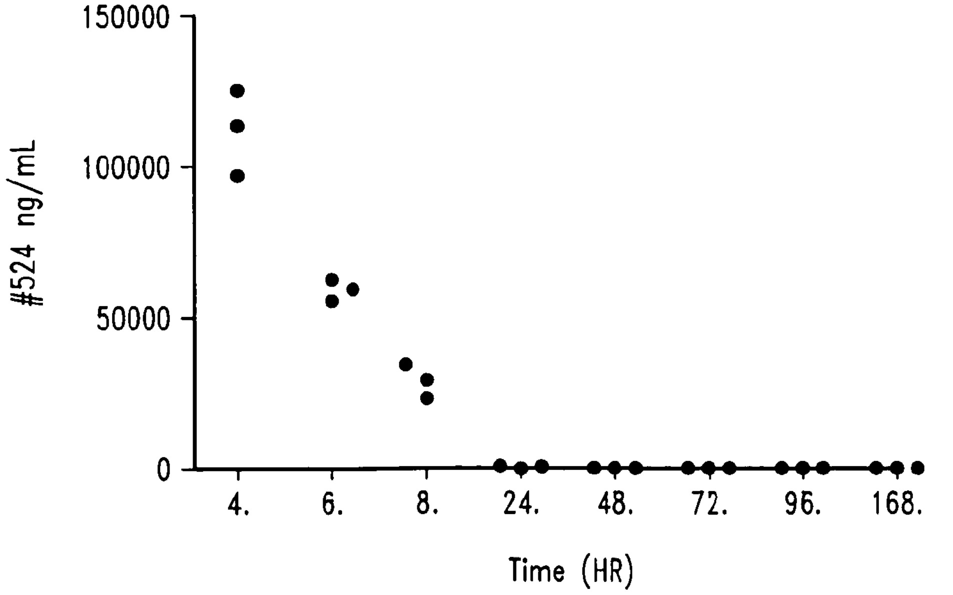
FIG. 14B shows the plasma clearance for the 20 mg/kg dose in individual animals of anti-miR-524* (SEQ ID NO: 79) over time.
Figure 15A:
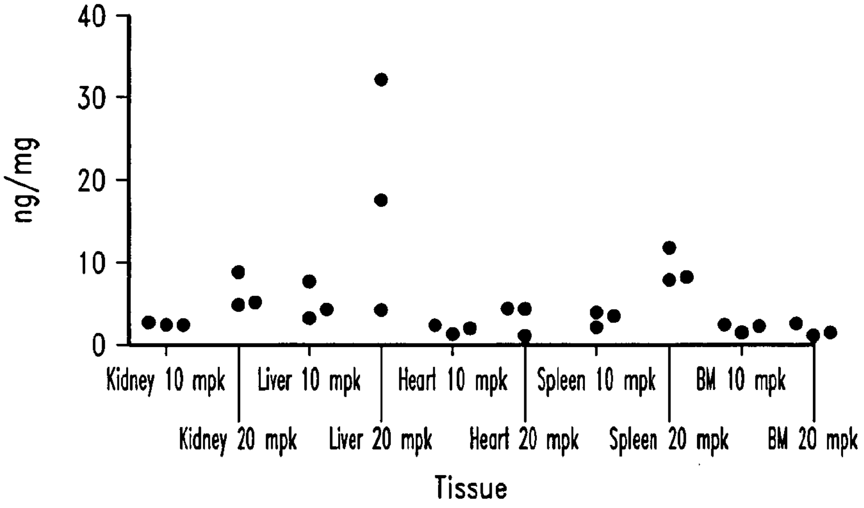
FIG. 15A shows the ng/mg of anti-miR-103-1,2 (SEQ ID NO: 78)
Figure 15B:
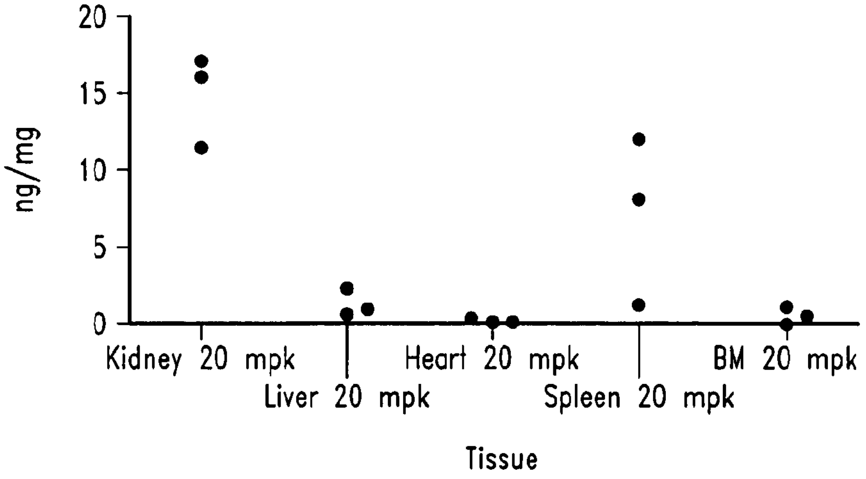
FIG. 15B shows the ng/mg of anti-miR-524* (SEQ ID NO: 79) in the tissues and at the dosage specified (mpk=milligrams per kilogram dosage of the anti-miRNA nucleic acid) at 168 hours post-administration.

FIG. 14A shows the plasma clearance of the 20 mg/kg dose for individual animals of anti-miR-103-1,2 (SEQ ID NO: 78) in ng/ml versus hours post-administration. FIG. 14B shows the plasma clearance of the 20 mg/kg dose for individual animals of anti-miR-524* (SEQ ID NO: 79) in ng/ml versus hours post-administration. FIG. 15A shows the ng/mg of anti-miR-103-1,2 (SEQ ID NO: 78) and FIG. 15B shows the ng/mg of anti-miR-524* (SEQ ID NO: 79) in the tissues and at the dosage specified (mpk=milligrams per kilogram dosage of the anti-miRNA nucleic acid) at 168 hours post-administration.

What is claimed is:

1. A method of increasing expression or secretion of erythropoietin by a cell, said method comprising introducing into said cell a nucleic acid hybridizable to an RNA molecule, wherein:

(a) said RNA molecule is miR-524, or precursors thereof; and (b) said nucleic acid (i) hybridizes under stringent conditions to said RNA molecule, or (ii) comprises a sequence having at least 95% sequence identity with SEQ ID NO: 79.

2. The method of claim 1, wherein said nucleic acid comprises a sequence with no more than a 4 nucleobase difference from SEQ ID NO: 79.

3. The method of claim 1, wherein said nucleic acid comprises a sequence having 100% sequence identity with SEQ ID NO: 79.

4. The method of claim 1, wherein said cell is a kidney cell, a liver cell, a spleen cell, or a bone marrow cell.

5. The method of claim 1, wherein said cell is a kidney cell.

6. The method of claim 5, wherein said cell is a human kidney cell.

7. The method of claim 1, wherein said cell forms part of an organ.

8. The method of claim 7, wherein said organ is a kidney, liver, or spleen.

9. The method of claim 7, wherein said organ is a kidney.

10. The method of claim 1, wherein said nucleic acid is at least 12 nucleobases in length.

11. The method of claim wherein said nucleic acid is 12 to 30 nucleobases in length.

12. The method of claim 1, wherein said nucleic acid comprises a modified internucleotide linkage selected from the group consisting of phosphoroamidate, phosphorothiate, phosphorodithioate, boranophosphate, alkylphosphonate, and methylinemethylimino.

13. The method of claim 1, wherein said nucleic acid comprises a modified nucleic acid unit selected from the group consisting of locked nucleic acid unit, 2-O-alkyl ribonucleic acid unit, 2'amine ribonucleic acid unit, peptide nucleic acid unit, 2'fluoro-ribo nucleic acid unit, morpholino nucleic acid unit, cyclohexane nucleic acid unit, and a tricyclonucleic acid unit.

14. The method of claim 13, wherein said nucleic acid comprises a modified nucleic acid unit selected from the group consisting of locked nucleic acid unit, 2'-O-methyl ribonucleic acid unit, and 2'O-methoxy-ethyl ribonucleic acid unit.

15. The method of claim 1, wherein said nucleic acid is a locked nucleic acid, a 2'-O-methyl ribonucleic acid, or a mixed nucleic acid-locked nucleic acid.

16. The method of claim 1, wherein said nucleic acid is a locked nucleic acid or a mixed nucleic acid-locked nucleic acid.

17. A method for enhancing erythropoiesis in a subject, increasing erythropoietin levels in a subject, or treating a subject in need thereof for anemia, hemophilia, or sickle cell disease, the method comprising administering to said subject an effective amount of a nucleic acid hybridizable to an RNA molecule, wherein:

(a) said RNA molecule is miR-524, and precursors thereof; and (b) said nucleic acid (i) hybridizes under stringent conditions to said RNA molecule, or (ii) comprises a sequence having at least 95% sequence identity with SEQ ID NO: 79.

18. The method of claim 17, wherein said nucleic acid comprises a sequence with no more than a 4 nucleobase difference from SEQ ID NO: 79.

19. The method of claim 17, wherein said nucleic acid comprises a sequence having 100% sequence identity with SEQ ID NO: 79.

20. The method of claim 17, wherein said subject is a mammal.

21. The method of claim 17, wherein said subject is a human.

22. The method of claim 17, wherein said nucleic acid is at least 12 nucleobases in length.

23. The method of claim 17, wherein said nucleic acid is 12 to 30 nucleobases in length.

24. The method of claim 17, wherein said nucleic acid comprises a modified internucleotide linkage selected from the group consisting of phosphoroamidate, phosphorothiate, phosphorodithioate, boranophosphate, alkylphosphonate, and methylinemethylimino.

25. The method of claim 17, wherein said nucleic, acid comprises a modified nucleic acid unit selected from the group consisting of locked nucleic acid unit, 2'-O-alkyl ribonucleic acid, unit, 2'amine ribonucleic acid unit, peptide nucleic acid unit, 2'fluoro-ribo nucleic acid unit, morpholino nucleic acid unit, cyclohexane nucleic acid unit, and a tricyclonucleic acid unit.

26. The method of claim 25, wherein said nucleic acid comprises a modified nucleic acid unit selected from the group consisting of locked nucleic acid unit, 2'-O-methyl ribonucleic acid unit, and 2'O-methoxy-ethyl ribonucleic acid unit.

27. The method of claim 17, wherein said nucleic acid is a locked nucleic acid, a 2'-O-methyl ribonucleic acid, or a mixed nucleic acid-locked nucleic acid.

28. The method of claim 17, wherein said nucleic, acid is a locked nucleic acid, or a mixed nucleic acid-locked nucleic acid.

* * * * *